US012298294B2

United States Patent
Maney, Jr.

(10) Patent No.: US 12,298,294 B2
(45) Date of Patent: May 13, 2025

(54) MULTIPLEXING ANALOG COMPONENTS IN BIOCHEMICAL SENSOR ARRAYS

(71) Applicant: Roche Sequencing Solutions, Inc., Pleasanton, CA (US)

(72) Inventor: J. William Maney, Jr., Emerald Hills, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 882 days.

(21) Appl. No.: 17/247,670

(22) Filed: Dec. 18, 2020

(65) Prior Publication Data

US 2021/0148886 A1    May 20, 2021

Related U.S. Application Data

(63) Continuation of application No. PCT/EP2019/067185, filed on Jun. 27, 2019.
(Continued)

(51) Int. Cl.
*G01N 33/487* (2006.01)
*B82Y 15/00* (2011.01)
(Continued)

(52) U.S. Cl.
CPC ..... *G01N 33/48721* (2013.01); *C12Q 1/6869* (2013.01); *G01N 27/228* (2013.01);
(Continued)

(58) Field of Classification Search
CPC .......... G01N 33/48721; G01N 27/228; G01N 27/4065; G01N 27/413; C12Q 1/6869;
(Continued)

(56) References Cited

U.S. PATENT DOCUMENTS

2012/0322679 A1* 12/2012 Brown ................. C12Q 1/6869
204/451
2013/0237460 A1* 9/2013 Deierling ......... G01N 27/44782
506/38
(Continued)

FOREIGN PATENT DOCUMENTS

CN        102741430        10/2012
CN        104303050 A       1/2015
(Continued)

OTHER PUBLICATIONS

Liu, F. et al., Lab-on-a-chip electrical multiplexing techniques for cellular and molecular biomarker detection, 2018, p. 021501, XP055612613, DOI: 10.1063/1.5022168, 12, No. 2,, Biomicrofluidics.
(Continued)

*Primary Examiner* — Luan V Van
*Assistant Examiner* — Shizhi Qian
(74) *Attorney, Agent, or Firm* — Kilpatrick Townsend and Stockton LLP

(57) ABSTRACT

Techniques for increasing the density and the number of cells on a nanopore sensor chip are disclosed. Two or more cells of the nanopore sensor chip share some analog components (e.g., an integration capacitor and/or a read-out transistor) through one or more digital relays. Under the control of various control signals during a sampling period of the sensor chip, the two or more cells are connected one at time to the shared analog components and are measured one at a time using the shared analog components. In this way, the average size of the cells on the sensor chip is reduced to increase the cell density without affecting the analog measurement performance of the cells.

20 Claims, 14 Drawing Sheets

Related U.S. Application Data

(60) Provisional application No. 62/690,816, filed on Jun. 27, 2018.

(51) Int. Cl.
  *C12Q 1/6869* (2018.01)
  *G01N 27/22* (2006.01)
  *G01N 27/406* (2006.01)
  *G01N 27/413* (2006.01)

(52) U.S. Cl.
  CPC ....... *G01N 27/4065* (2013.01); *G01N 27/413* (2013.01); *B82Y 15/00* (2013.01); *C12Q 2563/116* (2013.01); *C12Q 2565/631* (2013.01)

(58) Field of Classification Search
  CPC ........ C12Q 2563/116; C12Q 2565/631; B82Y 15/00
  See application file for complete search history.

(56) References Cited

U.S. PATENT DOCUMENTS

| | | | |
|---|---|---|---|
| 2015/0275287 A1* | 10/2015 | Tian | G01N 33/48721 205/780.5 |
| 2016/0169865 A1* | 6/2016 | Rosenstein | G01N 33/48721 204/600 |
| 2016/0178554 A1* | 6/2016 | Chen | G01N 27/44791 204/603 |
| 2016/0178577 A1* | 6/2016 | Chen | C12Q 1/6869 204/453 |
| 2016/0266064 A1 | 9/2016 | Deierling et al. | |
| 2016/0370313 A1* | 12/2016 | Aparin | G01N 21/27 |
| 2017/0038333 A1* | 2/2017 | Turner | C12Q 1/6874 |
| 2017/0059547 A1 | 3/2017 | Feng et al. | |
| 2018/0037948 A1 | 2/2018 | Mannion et al. | |
| 2018/0173844 A1 | 6/2018 | Fernandez-gomez | |

FOREIGN PATENT DOCUMENTS

| | | |
|---|---|---|
| CN | 105695318 A | 6/2016 |
| CN | 106029897 A | 10/2016 |
| CN | 107250780 A | 10/2017 |
| JP | 2013512447 A | 4/2013 |
| JP | 2017507653 A | 3/2017 |
| TW | I551863 B | 10/2016 |
| TW | I618932 B | 3/2018 |
| WO | 2010122293 A1 | 10/2010 |
| WO | 2011067559 A1 | 6/2011 |
| WO | 2015148127 A1 | 10/2015 |
| WO | 2016/100749 A1 | 6/2016 |
| WO | 2017220732 A1 | 12/2017 |

OTHER PUBLICATIONS

International Search Report and Written Opinion mailed Aug. 21, 2019 in connection with PCT/EP2019/067185 filed Jun. 27, 2019, 14 pages.

Zhang. Yin, Manufacturing,and Key Technology Research of Solid State Nanopore Single Molecule Sensors, Full Text Database of Chinese Doctoral Dissertations, Information Technology Section, Feb. 15, 2018, 121 pages (English Abstract), Southeast University, school of mechanical engineering, CN.

* cited by examiner

MULTIPLEXING ANALOG COMPONENTS IN BIOCHEMICAL SENSOR ARRAYS

CROSS REFERENCE TO RELATED APPLICATIONS

This application is a continuation of International Patent Application No. PCT/EP2019/067185, filed Jun. 27, 2019, which claims priority to U.S. Provisional Application No. 62/690,816, filed Jun. 27, 2018, each of which is incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Nanopore membrane devices having pore sizes on the order of one nanometer in internal diameter have shown promise in rapid nucleotide sequencing. When a voltage signal is applied across a nanopore immersed in a conducting fluid, the electric field can move ions in the conducting fluid through the nanopore. The movement of ions in the conducting fluid through the nanopore can cause a small ion current. The voltage applied can also move the molecules to be sequenced into, through, or out of the nanopore. The level of the ion current (or a corresponding voltage) depends on the sizes and chemical structures of the nanopore and the particular molecule that has been moved into the nanopore.

As an alternative to a DNA molecule (or other nucleic acid molecule to be sequenced) moving through the nanopore, a molecule (e.g., a nucleotide being added to a DNA strand) can include a particular tag of a particular size and/or structure. The ion current or a voltage in a circuit including the nanopore (e.g., at an integration capacitor) can be measured as a way of measuring the resistance of the nanopore corresponding to the molecule, thereby allowing the detection of the particular molecule in the nanopore and the particular nucleotide at a particular position of a nucleic acid.

In order to improve the throughput, a nanopore-based sequencing sensor chip can incorporate a large number of sensor cells configured as an array for parallel DNA sequencing. For example, a nanopore-based sequencing sensor chip may include 100,000 or more cells arranged in a two-dimensional array for sequencing 100,000 or more DNA molecules in parallel. It can be very difficult to fit so many cells into a sensor chip without compromising measurements.

BRIEF SUMMARY

Techniques described herein relate to sensor chips including a large number of biochemical sensor cells. One way to fit the large number of sensor cells on a chip while keeping the size of the chip under control is to reduce the area of each sensor cell. Each sensor cell may include multiple digital and analog components. Most digital components can be shrunk by using more advanced processing technologies, without affecting the performance of the sensor cell. Reducing the size of the analog components, on the other hand, may significantly affect the performance of the sensor cell. Certain embodiments disclosed herein can reduce the average size of the sensor cells by sharing some analog components (such as an integration capacitor and/or the read-out transistor) between two or more cells.

In one sampling period, each of the cells that share the same analog components may be precharged to a known voltage level, charged or discharged by a current passing through the nanopore, and sampled by a read-out circuit and an ADC during a fraction of the sampling period of the sensor chip. For example, if the sampling period is about 1 ms and the integration time is about 250 µs, four cells may share the same analog components and may be measured one at a time using the same analog components. A digital switch can be added to each cell for connecting the cell to the analog components, such as the integration capacitor and the readout transistor.

Because the analog components are shared among multiple cells, they can remain large to reduce noise (or offset) and achieve the desired performance. At the same time, the total number of analog components on the sensor chip can be reduced to, for example, one half, one quarter, or one eighth of the number of cells. Thus, the average size of the cells can be reduced to increase the cell density or the number of cells on the sensor chip without significantly affecting the performance of the cells.

In various embodiments, each cell may be controlled independently to precharge the integration capacitor to a desired voltage level by connecting the integration capacitor to the desired voltage level. A parasitic bilayer capacitor of the cell may be used as the integration capacitor and may be large enough for the noise performance, and thus no additional integration capacitor may be needed because adding the additional integration capacitor may reduce the voltage change on the integration capacitor or increase the integration time. It may be desirable to check whether the bilayer capacitor is functioning properly, but it may be difficult to perform the check without using an additional capacitor. Thus, in some implementations, a switch may be added to the circuit to disconnect the additional capacitor from the cell during the signal integration and to connect the additional capacitor to the cell for evaluation or verification purposes.

These and other embodiments of the invention are described in detail below. For example, other embodiments may be directed to systems, devices, methods, and computer readable media associated with the biochemical sensor chips described herein.

A better understanding of the nature and advantages of embodiments of the present invention may be gained with reference to the following detailed description and the accompanying drawings

DEFINITIONS

Figure 1:
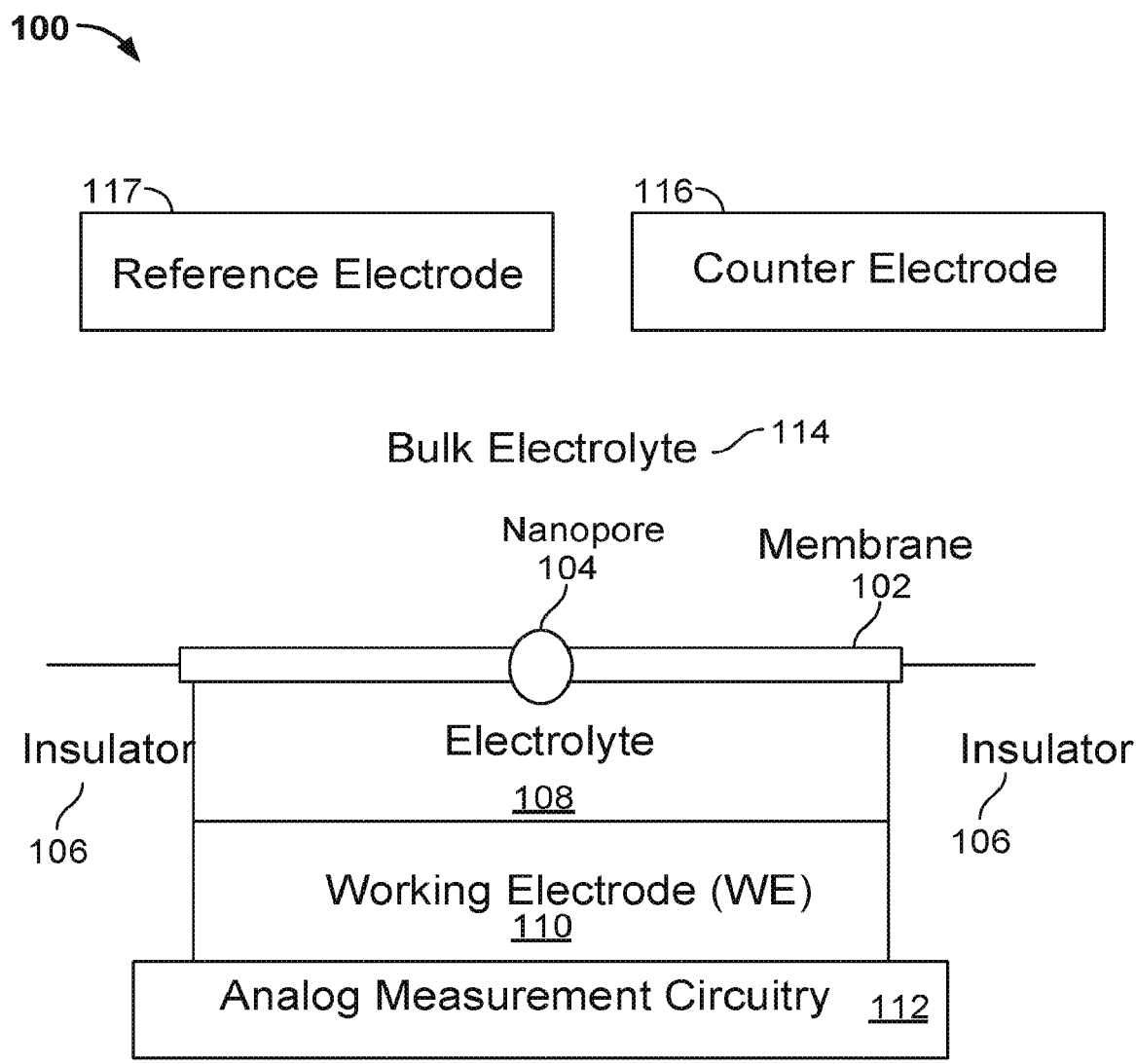
FIG. 1 is a simplified structure illustrating an embodiment of a nanopore cell on a nanopore-based sequencing chip.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs). The term nucleic acid may be used interchangeably with gene, cDNA, mRNA, oligonucleotide, and polynucleotide.

The term "template" may refer to a single stranded nucleic acid molecule that is copied into a complementary strand of DNA nucleotides for DNA synthesis. In some cases, a template may refer to the sequence of DNA that is copied during the synthesis of mRNA.

The term "primer" may refer to a short nucleic acid sequence that provides a starting point for DNA synthesis. Enzymes that catalyze the DNA synthesis, such as DNA polymerases, can add new nucleotides to a primer for DNA replication.

The term "Nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. Some nanopores are proteins.

As used herein, the term "column" may generally refer to nanopore cells in a nanopore cell array that share a sampling and conversion circuit. Nanopore cells in a column may be connected to a same column bus that connects to the sampling and conversion circuit. Nanopore cells in a column may or may not be physically fabricated in a column on a nanopore sensor chip.

As used herein, the term "bright period" may generally refer to the time period when a tag of a tagged nucleotide is forced into a nanopore by an electric field applied through an AC signal. The term "dark period" may generally refer to the time period when a tag of a tagged nucleotide is pushed out of the nanopore by the electric field applied through the AC signal. An AC cycle may include the bright period and the dark period. In different embodiments, the polarity of the voltage signal applied to a nanopore cell to put the nanopore cell into the bright period (or the dark period) may be different.

DETAILED DESCRIPTION

Techniques disclosed herein relate to nanopore-based nucleic acid sequencing, and more specifically, to increasing the cell density or increasing the number of nanopore cells on a nanopore-based sequencing sensor chip that includes a large number of parallel sequencing nanopore cells. In order to increase the throughput of the sensor chip, it is desirable to increase the number of cells in the sensor chip. The number of cells that can fit on a sensor chip may be limited by the minimum size of each cell, which may include some digital circuit components (e.g., SRAM or switches) and analog circuit components (e.g., capacitors, buffers, amplifiers, etc.). The minimum size of the cell may be limited by the size of the analog circuit components. Thus, to increase the density of cells on the sensor chip, the total area used by the analog circuit components needs to be reduced.

Certain techniques disclosed herein reduce the average size of the cells on a sensor chip by sharing some analog components (such as an integration capacitor and/or a read-out transistor) between two or more cells. For a nanopore-based sensor chip, the minimum sampling period may depend on the ADC bandwidth and the digital IO bandwidth, while the integration period for each cell may depend on the size of the integration capacitor in the cell. In general, the integration period for a single cell may be less than a half of the minimum sampling period. Therefore, each cell may only need to use the integration capacitor during a fraction of the sampling period, and thus can share the integration capacitor with one or more other cells. For example, if the sampling period is about 1 ms while the integration time is about 250 μs, four cells may share the same analog components. A small digital switch can be added to each cell to selectively connect the cell to the shared analog components, such as the integration capacitor and the readout transistor. As such, in one sampling period, each of the cells sharing the same analog components may be precharged, charged or discharged, and then sampled by a read-out circuit and an ADC during a fraction of the sampling period of the sensor chip.

In this way, the physical size of the analog components (e.g., the integration capacitors) can be kept as large as desired, and therefore may not affect the performance of the cell. Because the analog components are shared among multiple cells, the total number of analog components (e.g., integration capacitors) on the sensor chip can be reduced to, for example, one half, one quarter, or one eighth, of the number of cells. At the same time, the digital circuit components of the cells can be shrunk by using a more advanced fabrication process with a smaller critical dimension, without affecting the performance of the cell. Thus, the average size of the cells can be reduced. As such, the cell density or the number of cells on the sensor chip can be increased without affecting the performance of the cells.

I. Nanopore Based Sequencing Chip

A nanopore sensor chip may include an array of nanopore cells for biochemical analysis, such as nucleic acid sequencing. Each nanopore cell may include a nanopore formed or otherwise provided in a membrane. In some examples, the nanopore has a characteristic width or diameter on the order of 0.1 nanometers (nm) to about 1000 nm. The membrane can be an organic membrane, such as a lipid bilayer, or a synthetic membrane, such as a membrane formed of a polymeric material. Each cell may also include a control and sensing circuit integrated on a semiconductor substrate. Nanopore cells on a nanopore sensor chip may be implemented in many different ways.

A. Nanopore Sequencing Cell Structure

FIG. 1 is a simplified structure illustrating an embodiment of a nanopore cell 100 on a nanopore-based sequencing chip according to certain embodiments. Nanopore cell 100 may include a well (e.g., insulator 106) formed by dielectrical material, such as oxide. A membrane 102 may be formed over the surface of the well to cover the well. In some embodiments, membrane 102 may be a lipid bilayer. A bulk electrolyte 114 that may contain, for example, soluble protein nanopore transmembrane molecular complexes (PNTMC) and the analyte of interest, is placed onto the surface of the cell. A single PNTMC may be inserted into membrane 102 by electroporation to form a nanopore 104. Nanopore 104 may be formed in membrane 102 in other manners. The individual membranes in an array are neither chemically nor electrically connected to each other. Nanopore 104 operates on the analytes and modulates the ionic current through the otherwise impermeable bilayer. Thus, each cell in the array is an independent sequencing machine, producing data unique to the single polymer molecule associated with nanopore 104.

Analog measurement circuitry 112 is connected to a metal working electrode 110 covered by an electrolyte 108. The electrolyte 108 is isolated from the bulk electrolyte 114 by the ion-impermeable membrane 102. Nanopore 104 crosses membrane 102 and provides the only path for ionic current to flow from the bulk liquid to working electrode 110. Nanopore cell 100 also includes a counter electrode (CE) 116, which may be an electrochemical potential sensor. Nanopore cell 100 may also include a reference electrode 117.

Figure 2:
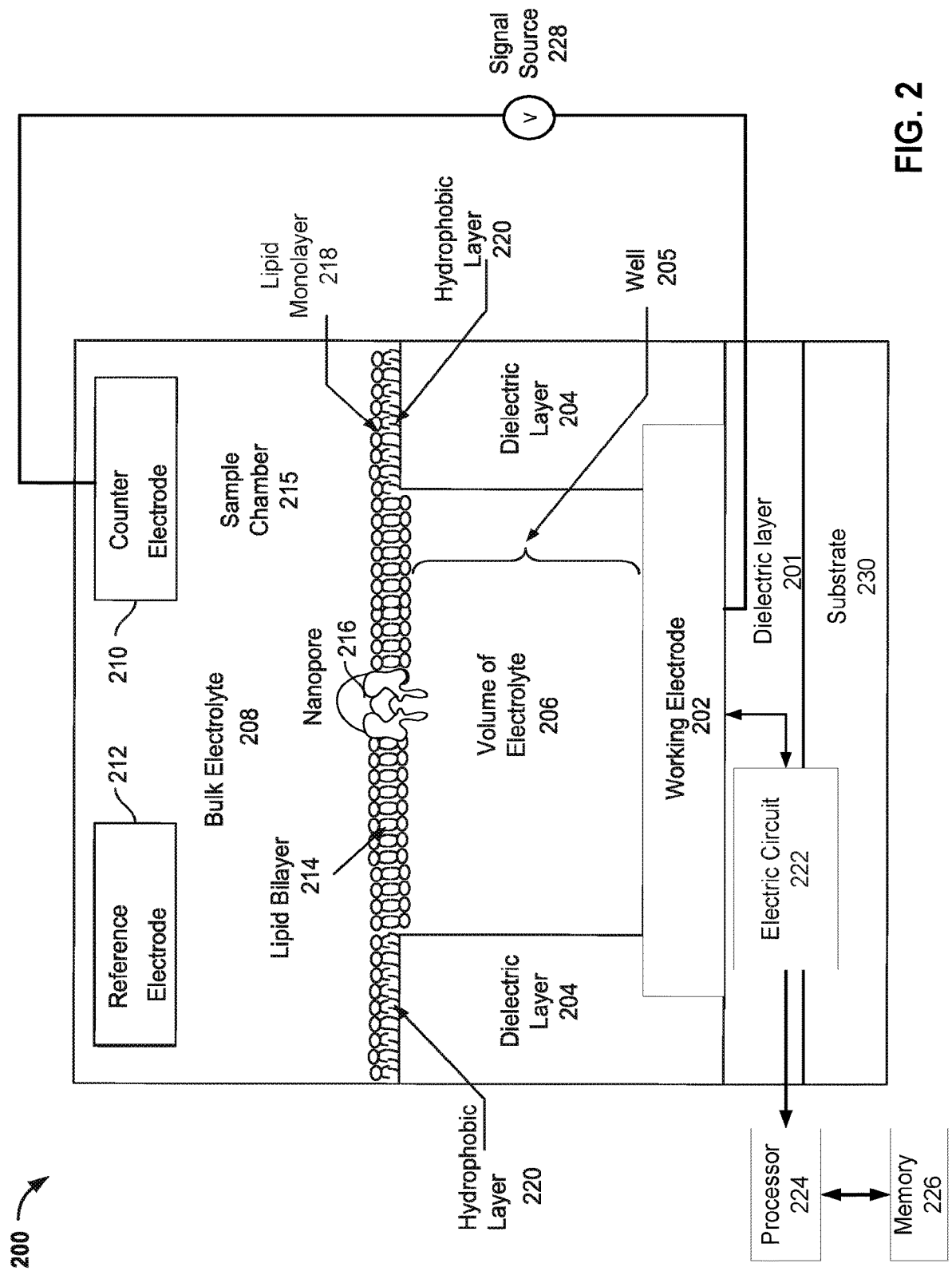
FIG. 2 illustrates an embodiment of a nanopore cell in a nanopore sensor chip that can be used to characterize a polynucleotide or a polypeptide.

FIG. 2 illustrates an embodiment of an example nanopore cell 200 in a nanopore sensor chip, such as nanopore cell 100 of FIG. 1, that can be used to characterize a polynucleotide or a polypeptide. Nanopore cell 200 may include a well 205 formed of dielectric layers 201 and 204; a membrane, such as a lipid bilayer 214 formed over well 205; and a sample chamber 215 on lipid bilayer 214 and separated from well 205 by lipid bilayer 214. Well 205 may contain a volume of electrolyte 206, and sample chamber 215 may hold bulk electrolyte 208 containing a nanopore, e.g., a soluble protein nanopore transmembrane molecular complexes (PNTMC), and the analyte of interest (e.g., a nucleic acid molecule to be sequenced).

Nanopore cell 200 may include a working electrode 202 at the bottom of well 205 and a counter electrode 210 disposed in sample chamber 215. A signal source 228 may apply a voltage signal between working electrode 202 and counter electrode 210. A single nanopore (e.g., a PNTMC) may be inserted into lipid bilayer 214 by an electroporation process caused by the voltage signal, thereby forming a nanopore 216 in lipid bilayer 214. The individual membranes (e.g., lipid bilayers 214 or other membrane structures) in the array may be neither chemically nor electrically connected to each other. Thus, each nanopore cell in the array may be an independent sequencing machine, producing data unique to the single polymer molecule associated with the nanopore that operates on the analyte of interest and modulates the ionic current through the otherwise impermeable lipid bilayer.

As shown in FIG. 2, nanopore cell 200 may be formed on a substrate 230, such as a silicon substrate. Dielectric layer 201 may be formed on substrate 230. Dielectric material used to form dielectric layer 201 may include, for example, glass, oxides, nitrides, and the like. An electric circuit 222 for controlling electrical stimulation and for processing the signal detected from nanopore cell 200 may be formed on substrate 230 and/or within dielectric layer 201. For example, a plurality of patterned metal layers (e.g., metal 1 to metal 6) may be formed in dielectric layer 201, and a plurality of active devices (e.g., transistors) may be fabricated on substrate 230. In some embodiments, signal source 228 is included as a part of electric circuit 222. Electric circuit 222 may include, for example, amplifiers, integrators, analog-to-digital converters, noise filters, feedback control logic, and/or various other components. Electric circuit 222 may be further coupled to a processor 224 that is coupled to a memory 226, where processor 224 can analyze the sequencing data to determine sequences of the polymer molecules that have been sequenced in the array.

Working electrode 202 may be formed on dielectric layer 201, and may form at least a part of the bottom of well 205. In some embodiments, working electrode 202 is a metal electrode. For non-faradaic conduction, working electrode 202 may be made of metals or other materials that are resistant to corrosion and oxidation, such as, for example, platinum, gold, titanium nitride, and graphite. For example, working electrode 202 may be a platinum electrode with electroplated platinum. In another example, working electrode 202 may be a titanium nitride (TiN) working electrode. Working electrode 202 may be porous, thereby increasing its surface area and a resulting capacitance associated with working electrode 202. Because the working electrode of a nanopore cell may be independent from the working electrode of another nanopore cell, the working electrode may be referred to as cell electrode in this disclosure.

Dielectric layer 204 may be formed above dielectric layer 201. Dielectric layer 204 forms the walls surrounding well 205. Dielectric material used to form dielectric layer 204 may include, for example, glass, oxide, silicon mononitride (SiN), polyimide, or other suitable hydrophobic insulating material. The top surface of dielectric layer 204 may be silanized. The silanization may form a hydrophobic layer 220 above the top surface of dielectric layer 204. In some embodiments, hydrophobic layer 220 has a thickness of about 1.5 nanometer (nm).

Well 205 formed by the dielectric layer 204 includes volume of electrolyte 206 above working electrode 202. Volume of electrolyte 206 may be buffered and may include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$). In some embodiments, volume of electrolyte 206 has a thickness of about three microns (μm).

As also shown in FIG. 2, a membrane may be formed on top of dielectric layer 204 and span across well 205. In some embodiments, the membrane may include a lipid monolayer 218 formed on top of hydrophobic layer 220. As the membrane reaches the opening of well 205, lipid monolayer may transition to lipid bilayer 214 that spans across the opening of well 205. The lipid bilayer may comprise or consist of phospholipid, for example, selected from diphytanoyl-phosphatidylcholine (DPhPC), 1,2-diphytanoyl-sn-glycero-3-phosphocholine, 1,2-Di-O-Phytanyl-sn-Glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy(polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy(polyethylene glycol)-2000]; 1,2-dioleoyl-sn-glycero-3-phosphoethanolamine-N-lactosyl; GM1 Ganglioside, Lysophosphatidylcholine (LPC) or any combination thereof.

As shown, lipid bilayer 214 is embedded with a single nanopore 216, e.g., formed by a single PNTMC. As described above, nanopore 216 may be formed by inserting a single PNTMC into lipid bilayer 214 by electroporation. Nanopore 216 may be large enough for passing at least a portion of the analyte of interest and/or small ions (e.g., $Na^+$, $K^+$, $Ca^{2+}$, $Cl^-$) between the two sides of lipid bilayer 214.

Sample chamber 215 is over lipid bilayer 214, and can hold a solution of the analyte of interest for characterization. The solution may be an aqueous solution containing bulk electrolyte 208 and buffered to an optimum ion concentration and maintained at an optimum pH to keep the nanopore 216 open. Nanopore 216 crosses lipid bilayer 214 and provides the only path for ionic flow from bulk electrolyte 208 to working electrode 202. In addition to nanopores (e.g., PNTMCs) and the analyte of interest, bulk electrolyte 208 may further include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

Counter electrode (CE) 210 may be an electrochemical potential sensor. In some embodiments, counter electrode 210 may be shared between a plurality of nanopore cells, and may therefore be referred to as a common electrode. In some cases, the common potential and the common electrode may be common to all nanopore cells, or at least all nanopore cells within a particular grouping. The common electrode can be configured to apply a common potential to the bulk electrolyte 208 in contact with the nanopore 216. Counter electrode 210 and working electrode 202 may be coupled to signal source 228 for providing electrical stimulus (e.g., voltage bias) across lipid bilayer 214, and may be used for sensing electrical characteristics of lipid bilayer 214 (e.g., resistance, capacitance, and ionic current flow). In some embodiments, nanopore cell 200 can also include a reference electrode 212.

In some embodiments, various checks can be made during creation of the nanopore cell as part of evaluation. Once a nanopore cell is created, further evaluation steps can be performed, e.g., to identify nanopore cells that are performing as desired (e.g., one nanopore in the cell). Such evaluation checks can include physical checks, voltage calibration, open channel calibration, and identification of cells with a single nanopore.

B. Detection Signals of Nanopore Sequencing Cell

Nanopore cells in nanopore sensor chip, such as nanopore cell 100, may enable parallel sequencing using a single molecule nanopore-based sequencing by synthesis (Nano-SBS) technique.

Figure 3:
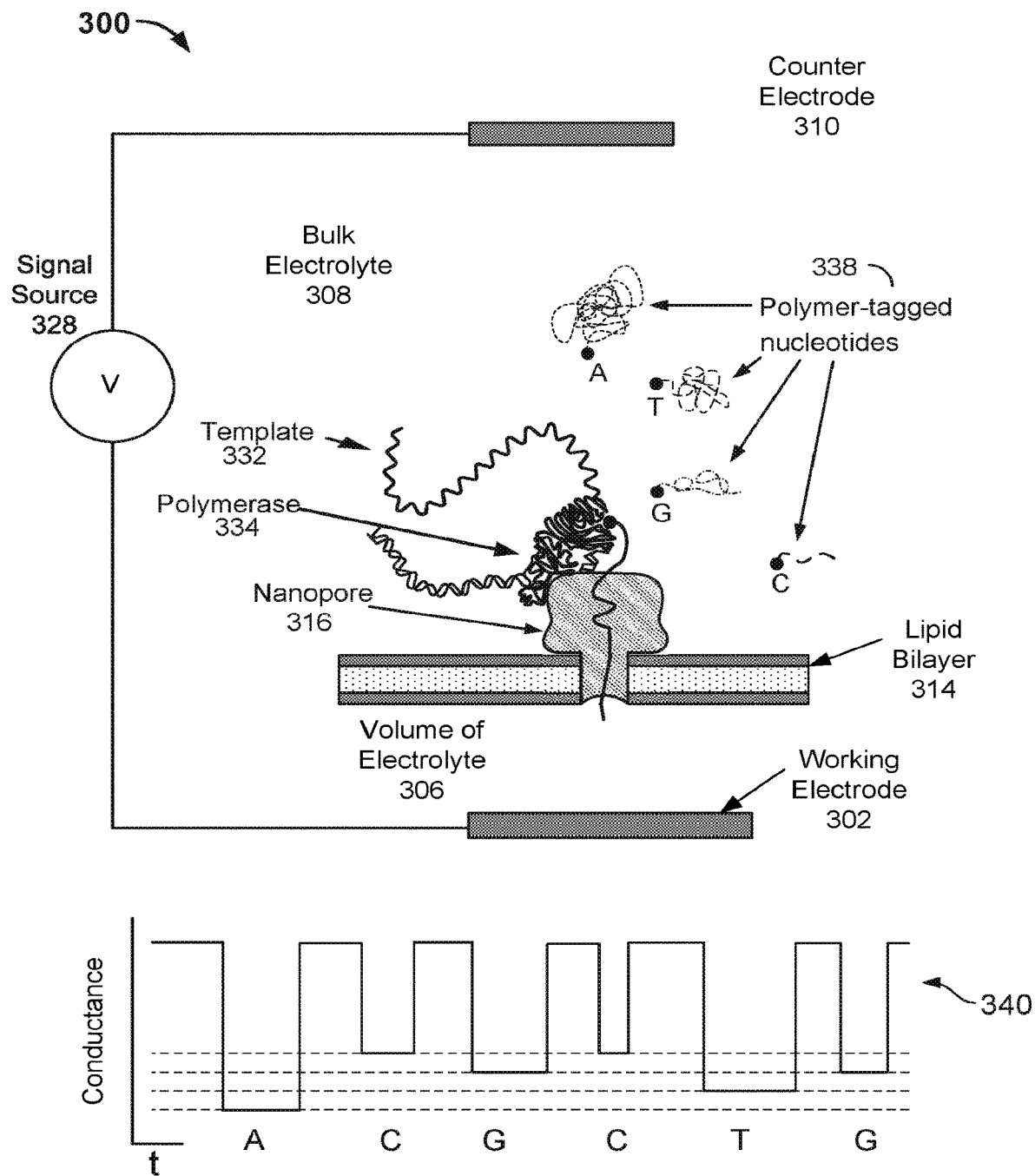
FIG. 3 illustrates an embodiment of a nanopore cell performing nucleotide sequencing using a nanopore-based sequencing-by-synthesis (Nano-SBS) technique.

FIG. 3 illustrates an embodiment of a nanopore cell 300 performing nucleotide sequencing using the Nano-SBS technique. In the Nano-SBS technique, a template 332 to be sequenced (e.g., a nucleotide acid molecule or another analyte of interest) and a primer may be introduced into bulk electrolyte 308 in the sample chamber of nanopore cell 300. As examples, template 332 can be circular or linear. A nucleic acid primer may be hybridized to a portion of template 332 to which four differently polymer-tagged nucleotides 338 may be added.

In some embodiments, an enzyme (e.g., a polymerase 334, such as a DNA polymerase) may be associated with nanopore 316 for use in the synthesizing a complementary strand to template 332. For example, polymerase 334 may be covalently attached to nanopore 316. Polymerase 334 may catalyze the incorporation of nucleotides 338 onto the primer using a single stranded nucleic acid molecule as the template. Nucleotides 338 may comprise tag species ("tags") with the nucleotide being one of four different types: A, T, G, or C. When a tagged nucleotide is correctly complexed with polymerase 334, the tag may be pulled (loaded) into the nanopore by an electrical force, such as a force generated in the presence of an electric field generated by a voltage applied across lipid bilayer 314 and/or nanopore 316. The tail of the tag may be positioned in the barrel of nanopore 316. The tag held in the barrel of nanopore 316 may generate a unique ionic blockade signal 340 due to the tag's distinct chemical structure and/or size, thereby electronically identifying the added base to which the tag attaches.

As used herein, a "loaded" or "threaded" tag may be one that is positioned in and/or remains in or near the nanopore for an appreciable amount of time, e.g., 0.1 millisecond (ms) to 10000 ms. In some cases, a tag is loaded in the nanopore prior to being released from the nucleotide. In some instances, the probability of a loaded tag passing through (and/or being detected by) the nanopore after being released upon a nucleotide incorporation event is suitably high, e.g., 90% to 99%.

In some embodiments, before polymerase 334 is connected to nanopore 316, the conductance of nanopore 316 may be high, such as, for example, about 300 picosiemens (300 pS). As the tag is loaded in the nanopore, a unique conductance signal (e.g., signal 340) is generated due to the tag's distinct chemical structure and/or size. For example, the conductance of the nanopore can be about 60 pS, 80 pS, 100 pS, or 120 pS, each corresponding to one of the four types of tagged nucleotides. The polymerase may then undergo an isomerization and a transphosphorylation reaction to incorporate the nucleotide into the growing nucleic acid molecule and release the tag molecule.

In some cases, some of the tagged nucleotides may not match (complementary bases) with a current position of the nucleic acid molecule (template). The tagged nucleotides that are not base-paired with the nucleic acid molecule may also pass through the nanopore. These non-paired nucleotides can be rejected by the polymerase within a time scale that is shorter than the time scale for which correctly paired nucleotides remain associated with the polymerase. Tags bound to non-paired nucleotides may pass through the nanopore quickly, and be detected for a short period of time (e.g., less than 10 ms), while tags bounded to paired nucleotides can be loaded into the nanopore and detected for a long period of time (e.g., at least 10 ms). Therefore, non-paired nucleotides may be identified by a downstream processor based at least in part on the time for which the nucleotide is detected in the nanopore.

A conductance (or equivalently the resistance) of the nanopore including the loaded (threaded) tag can be measured via a current passing through the nanopore, thereby providing an identification of the tag species and thus the nucleotide at the current position. In some embodiments, a direct current (DC) signal can be applied to the nanopore cell (e.g., so that the direction at which the tag moves through the nanopore is not reversed). However, operating a nanopore sensor for long periods of time using a direct current can change the composition of the electrode, unbalance the ion concentrations across the nanopore, and have other undesirable effects that can affect the lifetime of the nanopore cell. Applying an alternating current (AC) waveform can reduce the electro-migration to avoid these undesirable effects and have certain advantages as described below. The nucleic acid sequencing methods described herein that utilize tagged nucleotides are fully compatible with applied AC voltages, and therefore an AC waveform can be used to achieve these advantages.

The ability to re-charge the electrode during the AC detection cycle can be advantageous when sacrificial electrodes, electrodes that change molecular character in the current-carrying reactions (e.g., electrodes comprising silver), or electrodes that change molecular character in current-carrying reactions are used. An electrode may deplete during a detection cycle when a direct current signal is used. The recharging can prevent the electrode from reaching a depletion limit, such as becoming fully depleted, which can be a problem when the electrodes are small (e.g., when the electrodes are small enough to provide an array of electrodes having at least 500 electrodes per square millimeter). Electrode lifetime in some cases scales with, and is at least partly dependent on, the width of the electrode.

Suitable conditions for measuring ionic currents passing through the nanopores are known in the art and examples are provided herein. The measurement may be carried out with a voltage applied across the membrane and pore. In some embodiments, the voltage used may range from −400 mV to +400 mV. The voltage used is preferably in a range having a lower limit selected from −400 mV, −300 mV, −200 mV, −150 mV, −100 mV, −50 mV, −20 mV, and 0 mV, and an upper limit independently selected from +10 mV, +20 mV, +50 mV, +100 mV, +150 mV, +200 mV, +300 mV, and +400 mV. The voltage used may be more preferably in the range of 100 mV to 240 mV and most preferably in the range of 160 mV to 240 mV. It is possible to increase discrimination between different nucleotides by a nanopore using an increased applied potential. Sequencing nucleic acids using AC waveforms and tagged nucleotides is described in US Patent Publication No. US 2014/0134616 entitled "Nucleic Acid Sequencing Using Tags," filed on Nov. 6, 2013, which is herein incorporated by reference in its entirety. In addition to the tagged nucleotides described in US 2014/0134616, sequencing can be performed using nucleotide analogs that lack a sugar or acyclic moiety, e.g., (S)-Glycerol nucleoside triphosphates (gNTPs) of the five common nucleobases: adenine, cytosine, guanine, uracil, and thymine (Horhota et al., Organic Letters, 8:5345-5347 [2006]).

Nanopore cells in a nanopore sensor chip may be implemented or used in many different ways. For example, in some embodiments, tags of different sizes and/or chemical structures may be attached to different nucleotides in a nucleic acid molecule to be sequenced. In some embodiments, a complementary strand to a template of the nucleic acid molecule to be sequenced may be synthesized by hybridizing differently polymer-tagged nucleotides with the template. In some implementations, the nucleic acid molecule and the attached tags may both move through the nanopore, and an ion current passing through the nanopore may indicate the nucleotide that is in the nanopore because of the particular size and/or structure of the tag attached to the nucleotide. In some implementations, only the tags may be moved into the nanopore. There may also be many different ways to detect the different tags in the nanopores.

C. Electric Circuit of Nanopore Sequencing Cell

Figure 4:
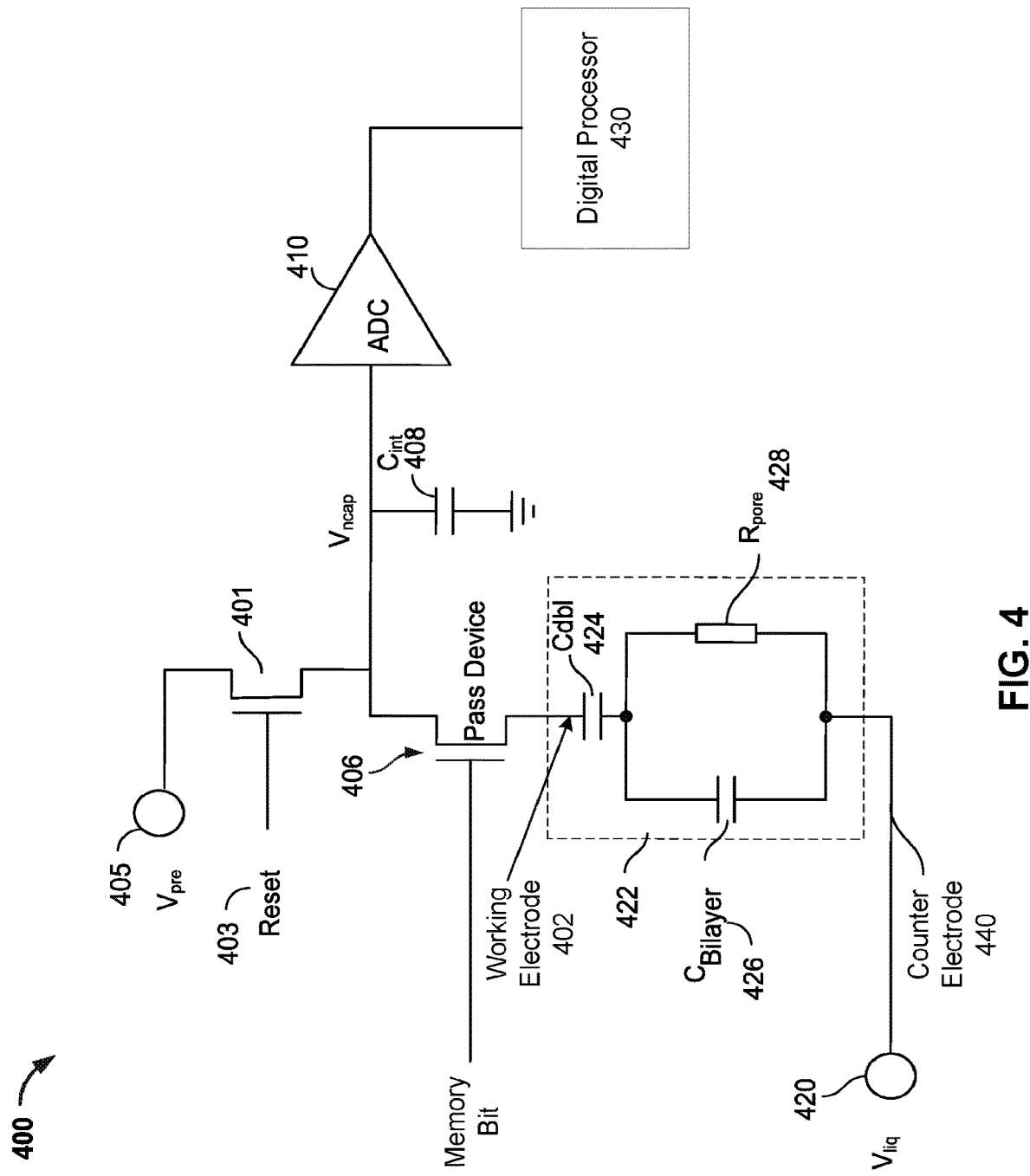
FIG. 4 illustrates an embodiment of an electric circuit representing an electrical model of a nanopore cell.

FIG. 4 illustrates an embodiment of an electric circuit 400 (which may include portions of electric circuit 222 in FIG. 2) representing an electrical model of a nanopore cell, such as nanopore cell 200. As described above, in some embodiments, electric circuit 400 includes a counter electrode 440 (e.g., counter electrode 210) that may be shared between a plurality of nanopore cells or all nanopore cells in a nanopore sensor chip, and may therefore also be referred to as a common electrode. The common electrode can be configured to apply a common potential to the bulk electrolyte (e.g., bulk electrolyte 208) in contact with the lipid bilayer (e.g., lipid bilayer 214) in the nanopore cells by connecting to a voltage source $V_{liq}$ 420. In some embodiments, an AC non-Faradaic mode may be utilized to modulate voltage $V_{liq}$ with an AC signal (e.g., a square wave) and apply it to the bulk electrolyte in contact with the lipid bilayer in the nanopore cell. In some embodiments, $V_{liq}$ is a square wave with a magnitude of ±200-250 mV and a frequency between, for example, 25 and 400 Hz. The bulk electrolyte between counter electrode 440 and the lipid bilayer may be modeled by a large capacitor (not shown), such as 100 µF or larger.

FIG. 4 also shows an electrical model 422 representing the electrical properties of a working electrode 402 (e.g., working electrode 202) and the lipid bilayer (e.g., lipid bilayer 214), according to certain embodiments. Electrical model 422 includes a capacitor 426 ($C_{Bilayer}$) that models a capacitance associated with the lipid bilayer and a resistor $R_{pore}$ 428 that models a variable resistance associated with the nanopore, which can change based on the presence of a particular tag in the nanopore. Electrical model 422 also includes a capacitor $C_{dbl}$ 424 having a double-layer capacitance $c_{dbl}$ and representing the electrical properties of working electrode 402 and the well (e.g., well 205) of the cell. Working electrode 402 may be configured to apply a distinct potential independent from the working electrodes in other nanopore cells.

Pass device 406 may be a switch that can be used to connect or disconnect the lipid bilayer and the working electrode from electric circuit 400. Pass device 406 may be controlled by a memory bit to enable or disable a voltage stimulus to be applied across the lipid bilayer in the nanopore cell. Before lipids are deposited to form the lipid bilayer, the impedance between the two electrodes may be very low because the well of the nanopore cell is not sealed, and therefore pass device 406 may be kept open to avoid a short-circuit condition. Pass device 406 may be closed after lipid solvent has been deposited to the nanopore cell to seal the well of the nanopore cell.

Electric circuit 400 may further include an on-chip integration capacitor $C_{int}$ 408 ($n_{cap}$). Integration capacitor $C_{int}$ 408 may be precharged by using a reset signal 403 to close switch 401, such that integration capacitor $C_{int}$ 408 is connected to a voltage source $V_{pre}$ 405. In some embodiments, voltage source $V_{pre}$ 405 provides a constant positive voltage with a magnitude of, for example, 900 mV. When switch 401 is closed, integration capacitor $C_{int}$ 408 may be precharged to the positive voltage level of voltage source $V_{pre}$ 405.

After integration capacitor $C_{int}$ 408 is precharged, reset signal 403 may be used to open switch 401 such that integration capacitor $C_{int}$ 408 is disconnected from voltage source $V_{pre}$ 405. At this point, depending on the level of voltage source $V_{liq}$, the potential of counter electrode 440 may be at a level higher than the potential of working electrode 402 (and integration capacitor $C_{int}$ 408), or vice versa. For example, during a positive phase of a square wave from voltage source $V_{liq}$ (e.g., the bright or dark period of the AC voltage source signal cycle), the potential of counter electrode 440 is at a level higher than the potential of working electrode 402. During a negative phase of the square wave from voltage source $V_{liq}$ (e.g., the dark or bright period of the AC voltage source signal cycle), the potential of counter electrode 440 is at a level lower than the potential of working electrode 402. Thus, in some embodiments, integration capacitor $C_{int}$ 408 may be further charged during the bright period from the precharged voltage level of voltage source $V_{pre}$ 405 to a higher level, and discharged during the dark period to a lower level, due to the potential difference between counter electrode 440 and working electrode 402. In other embodiments, the charging and discharging may occur in dark periods and bright periods, respectively.

Integration capacitor $C_{int}$ 408 may be charged or discharged for a fixed period of time, depending on the sampling rate of an analog-to-digital converter (ADC) 410, which may be higher than 1 kHz, 4 kHz, 10 kHz, 100 kHz, or more. For example, with a sampling rate of 1 kHz, integration capacitor $C_{int}$ 408 may be charged/discharged for a period of about 1 ms, and then the voltage level may be sampled and converted by ADC 410 at the end of the integration period. A particular voltage level would correspond to a particular tag species in the nanopore, and thus correspond to the nucleotide at a current position on the template.

After being sampled by ADC 410, integration capacitor $C_{int}$ 408 may be precharged again by using reset signal 403 to close switch 401, such that integration capacitor $C_{int}$ 408 is connected to voltage source $V_{pre}$ 405 again. The steps of pre-charging integration capacitor $C_{int}$ 408, waiting for a fixed period of time for integration capacitor $C_{int}$ 408 to charge or discharge, and sampling and converting the voltage level of integration capacitor by ADC 410 can be repeated in cycles throughout the sequencing process.

A digital processor 430 can process the ADC output data, e.g., for normalization, data buffering, data filtering, data compression, data reduction, event extraction, or assembling ADC output data from the array of nanopore cells into various data frames. In some embodiments, digital processor 430 can perform further downstream processing, such as base determination. Digital processor 430 can be implemented as hardware (e.g., in a GPU, FPGA, ASIC, etc.) or as a combination of hardware and software.

Accordingly, the voltage signal applied across the nanopore can be used to detect particular states of the nanopore. One of the possible states of the nanopore is an open-channel state when a tag-attached polyphosphate is absent from the barrel of the nanopore. Another four possible states of the nanopore each correspond to a state when one of the four different types of tag-attached polyphosphate nucleotides (A, T, G, or C) is held in the barrel of the nanopore. Yet another possible state of the nanopore is when the lipid bilayer is ruptured.

When the voltage level on integration capacitor $C_{int}$ 408 is measured after a fixed period of time, the different states of a nanopore may result in measurements of different voltage levels. This is because the rate of the voltage decay (decrease by discharging or increase by charging) on integration capacitor $C_{int}$ 408 (i.e., the steepness of the slope of a voltage on integration capacitor $C_{int}$ 408 versus time plot) depends on the nanopore resistance (e.g., the resistance of resistor $R_{pore}$ 428). More particularly, as the resistance associated with the nanopore in different states is different due to the molecules' (tags') distinct chemical structures, different corresponding rates of voltage decay may be observed and may be used to identify the different states of the nanopore. The voltage decay curve may be an exponential curve with an RC time constant $\tau=RC$, where R is the resistance associated with the nanopore (i.e., $R_{pore}$ 428) and C is the capacitance associated with the membrane (i.e., capacitor 426 ($C_{Bilayer}$)) in parallel with R. A time constant of the nanopore cell can be, for example, about 200-500 ms. The decay curve may not fit exactly to an exponential curve due to the detailed implementation of the bilayer, but the decay curve may be similar to an exponential curve and is monotonic, thus allowing detection of tags.

In some embodiments, the resistance associated with the nanopore in an open-channel state may be in the range of 100 MOhm to 20 GOhm. In some embodiments, the resistance associated with the nanopore in a state where a tag is inside the barrel of the nanopore may be within the range of 200 MOhm to 40 GOhm. In other embodiments, integration capacitor $C_{int}$ 408 may be omitted, as the voltage leading to ADC 410 will still vary due to the voltage decay in electrical model 422.

The rate of the decay of the voltage on integration capacitor $C_{int}$ 408 may be determined in different ways. As explained above, the rate of the voltage decay may be determined by measuring a voltage decay during a fixed time interval. For example, the voltage on integration capacitor $C_{int}$ 408 may be first measured by ADC 410 at time t1, and then the voltage is measured again by ADC 410 at time t2. The voltage difference is greater when the slope of the voltage on integration capacitor $C_{int}$ 408 versus time curve is steeper, and the voltage difference is smaller when the slope of the voltage curve is less steep. Thus, the voltage difference may be used as a metric for determining the rate of the decay of the voltage on integration capacitor $C_{int}$ 408, and thus the state of the nanopore cell.

In other embodiments, the rate of the voltage decay can be determined by measuring a time duration that is required for a selected amount of voltage decay. For example, the time required for the voltage to drop or increase from a first voltage level V1 to a second voltage level V2 may be measured. The time required is less when the slope of the voltage vs. time curve is steeper, and the time required is greater when the slope of the voltage vs. time curve is less steep. Thus, the measured time required may be used as a metric for determining the rate of the decay of the voltage $V_{ncap}$ on integration capacitor $C_{int}$ 408, and thus the state of the nanopore cell. One skilled in the art will appreciate the various circuits that can be used to measure the resistance of the nanopore, e.g., including current measurement techniques.

In some embodiments, electric circuit 400 may not include a pass device (e.g., pass device 406) and an extra capacitor (e.g., integration capacitor $C_{int}$ 408) that are fabricated on-chip, thereby facilitating the reduction in size of the nanopore-based sequencing chip. Due to the thin nature of the membrane (lipid bilayer), the capacitance associated with the membrane (e.g., capacitor 426 ($C_{Bilayer}$)) alone can suffice to create the required RC time constant without the need for additional on-chip capacitance. Therefore, capacitor 426 may be used as the integration capacitor, and may be precharged by the voltage signal $V_{pre}$ and subsequently be discharged or charged by the voltage signal $V_{liq}$. The elimination of the extra capacitor and the pass device that are otherwise fabricated on-chip in the electric circuit can significantly reduce the footprint of a single nanopore cell in the nanopore sequencing chip, thereby facilitating the scaling of the nanopore sequencing chip to include more and more cells (e.g., having millions of cells in a nanopore sequencing chip).

D. Data Sampling in Nanopore Cell

To perform sequencing of a nucleic acid, the voltage level of integration capacitor (e.g., integration capacitor $C_{int}$ 408 or capacitor 426 ($C_{Bilayer}$)) can be sampled and converted by the ADC (e.g., ADC 410) while a tagged nucleotide is being added to the nucleic acid. The tag of the nucleotide can be pushed into the barrel of the nanopore by the electric field across the nanopore that is applied through the counter electrode and the working electrode, for example, when the applied voltage is such that $V_{liq}$ is lower than $V_{pre}$.

1. Threading

A threading event is when a tagged nucleotide is attached to the template (e.g., nucleic acid fragment), and the tag goes in and out of the barrel of the nanopore. This can happen multiple times during a threading event. When the tag is in the barrel of the nanopore, the resistance of the nanopore may be higher, and a lower current may flow through the nanopore.

During sequencing, a tag may not be in the nanopore in some AC cycles (referred to as an open-channel state), where the current is the highest because of the lower resistance of the nanopore. When a tag is attracted into the barrel of the nanopore, the nanopore is in a bright mode. When the tag is pushed out of the barrel of the nanopore, the nanopore is in a dark mode.

2. Bright and Dark Period

During an AC cycle, the voltage on integration capacitor may be sampled multiple times by the ADC. For example, in one embodiment, an AC voltage signal is applied across the system at, e.g., about 100 Hz, and an acquisition rate of the ADC can be about 2000 Hz per cell. Thus, there can be about 20 data points (voltage measurements) captured per AC cycle (cycle of an AC waveform). Data points corresponding to one cycle of the AC waveform may be referred to as a set. In a set of data points for an AC cycle, there may be a subset captured when, for example, $V_{liq}$ is lower than $V_{pre}$, which may correspond to a bright mode (period) where the tag is forced into the barrel of the nanopore. Another subset may correspond to a dark mode (period) where the tag is pushed out of the barrel of the nanopore by the applied electric field when, for example, $V_{liq}$ is higher than $V_{pre}$.

3. Measured Voltages

For each data point, when the switch 401 is opened, the voltage at the integration capacitor (e.g., integration capacitor $C_{int}$ 408 or capacitor 426 ($C_{Bilayer}$)) will change in a decaying manner as a result of the charging/discharging by $V_{liq}$, e.g., as an increase from $V_{pre}$ to $V_{liq}$ when $V_{liq}$ is higher than $V_{pre}$ or a decrease from $V_{pre}$ to $V_{liq}$ when $V_{liq}$ is lower than $V_{pre}$. The final voltage values may deviate from $V_{liq}$ as the working electrode charges. The rate of change of the voltage level on the integration capacitor may be governed by the value of the resistance of the bilayer, which may include the nanopore, which may in turn include a molecule (e.g., a tag of a tagged nucleotide) in the nanopore. The voltage level can be measured at a predetermined time after switch 401 opens.

Switch 401 may operate at the rate of data acquisition. Switch 401 may be closed for a relatively short time period between two acquisitions of data, typically right after a measurement by the ADC. The switch allows multiple data points to be collected during each sub-period (bright or dark) of each AC cycle of $V_{liq}$. If switch 401 remains open, the voltage level on the integration capacitor, and thus the output value of the ADC, would fully decay and stay there. Instead, when switch 401 is closed, the integration capacitor is precharged again (to $V_{pre}$) and becomes ready for another measurement. Thus, switch 401 allows multiple data points to be collected for each sub-period (bright or dark) of each AC cycle. Such multiple measurements can allow higher resolution with a fixed ADC (e.g. 8-bit to 14-bit due to the greater number of measurements, which may be averaged). The multiple measurements can also provide kinetic information about the molecule threaded into the nanopore. The timing information may allow the determination of how long a threading takes place. This can also be used in helping to determine whether multiple nucleotides that are added to the nucleic acid strand are being sequenced.

Figure 5:
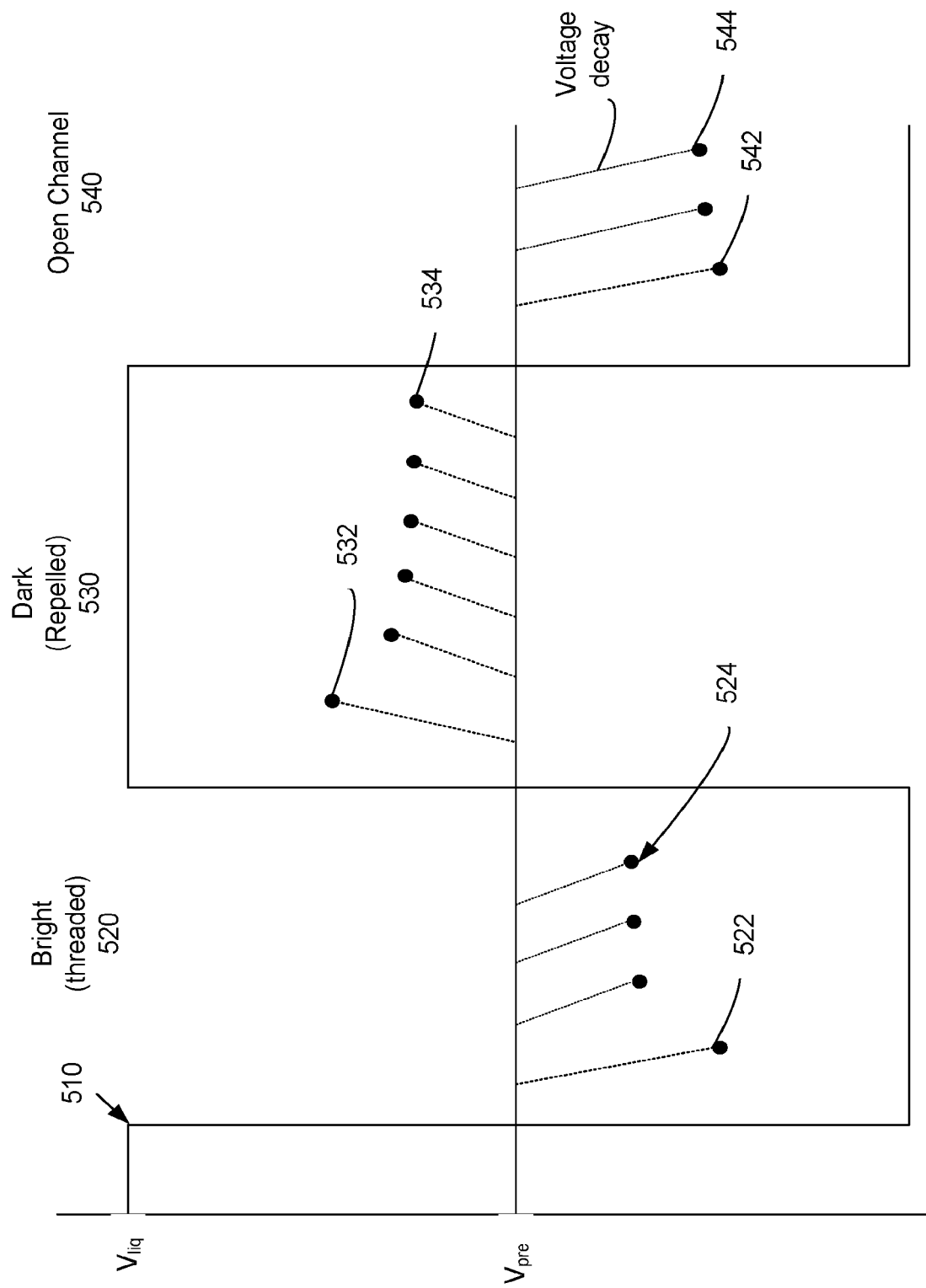
FIG. 5 shows example data points captured from a nanopore cell during bright periods and dark periods of AC cycles.

FIG. 5 shows example data points captured from an example nanopore cell during bright periods and dark periods of AC cycles. The voltage ($V_{pre}$) applied to the working electrode or the integration capacitor is at a constant level, such as 500 mV. A voltage signal 510 ($V_{liq}$) applied to the counter electrode of the nanopore cells is an AC signal shown as a rectangular wave, where the duty cycle may be any suitable value, such as less than or equal to 50%, for example, about 40%. In FIG. 5, the change in the data points is exaggerated (at a different scale from $V_{liq}$) for illustration purpose.

During a bright period 520, voltage signal 510 ($V_{liq}$) applied to the counter electrode is lower than the voltage $V_{pre}$ applied to the working electrode, such that a tag may be forced into the barrel of the nanopore by the electric field caused by the different voltage levels applied at the working electrode and the counter electrode (e.g., due to the charge on the tag and/or flow of the ions). When switch 401 is opened, the voltage at a node before the ADC (e.g., at an integration capacitor) will decrease. After a voltage data point is captured (e.g., after a specified time period), switch 401 may be closed and the voltage at the measurement node will increase back to $V_{pre}$ again. The process can repeat to measure multiple voltage data points. In this way, multiple data points may be captured during the bright period.

As shown in FIG. 5, a first data point 522 (also referred to as first point delta (FPD)) in the bright period after a change in the sign of the $V_{liq}$ signal may be lower than subsequent data points 524. This may be because there is no tag in the nanopore (open channel), and thus it has a low resistance and a high discharge rate. Data points 524 may be captured after a threading event has occurred, i.e., a tag is forced into the barrel of the nanopore, where the resistance of the nanopore and thus the rate of discharging of the integration capacitor depends on the particular type of tag that is forced into the barrel of the nanopore. Data points 524 may decrease slightly for each measurement due to charge built up at the double-layer capacitor (e.g., $C_{dbl}$ 424), as mentioned below.

During a dark period 530, voltage signal 510 ($V_{liq}$) applied to the counter electrode is higher than the voltage ($V_{pre}$) applied to the working electrode, such that any tag would be pushed out of the barrel of the nanopore. When switch 401 is opened, the voltage at the measurement node increases because the voltage level of voltage signal 510 ($V_{liq}$) is higher than $V_{pre}$. After a voltage data point is captured (e.g., after a specified time period), switch 401 may be closed and the voltage at the measurement node will decrease back to $V_{pre}$ again. The process can repeat to measure multiple voltage data points. Thus, multiple data points may be captured during the dark period, including a first point delta 532 and subsequent data points 534. As described above, during the dark period, any nucleotide tag is pushed out of the nanopore, and thus minimal information about any nucleotide tag is obtained, besides for use in normalization. Therefore, the output voltage signals from the cells during the dark period may have little or no use.

FIG. 5 also shows that during bright period 540, even though voltage signal 510 ($V_{liq}$) applied to the counter electrode is lower than the voltage ($V_{pre}$) applied to the working electrode, no threading event occurs (open-channel). Thus, the resistance of the nanopore is low, and the rate of discharging of the integration capacitor is high. As a result, the captured data points, including a first data point 542 and subsequent data points 544, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double-layer capacitor $C_{dbl}$. This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 5. Thus, it may desirable to measure the double-layer capacitance for data normalization and baseline adjustment in order to more accurately determine the bases associated with the measured voltage levels.

4. Determining Bases

For each usable nanopore cell of the nanopore sensor chip, a production mode can be run to sequence nucleic acids. The ADC output data captured during the sequencing can be normalized to provide greater accuracy. Normalization can account for offset effects, such as cycle shape and baseline shift. After normalization, embodiments can determine clusters of voltages for the threaded channels, where each cluster corresponds to a different tag species, and thus a different nucleotide. The clusters can be used to determine probabilities of a given voltage corresponding to a given nucleotide. As another example, the clusters can be used to determine cutoff voltages for discriminating between different nucleotides (bases).

Further details regarding the sequencing operation can be found in, for example, U.S. Patent Publication No. 2016/0178577 entitled "Nanopore-Based Sequencing With Varying Voltage Stimulus," U.S. Patent Publication No. 2016/0178554 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation."

II. Nanopore Cell Array

When the sequencing nanopore cells are arranged on the nanopore sensor chip, many nucleic acid molecules can be sequenced in parallel. Each cell can have some dedicated circuitry (e.g., an integration capacitor), but also can share some circuitry, e.g., an ADC, a signal source, an electrode, or a control circuit.

Figure 6:
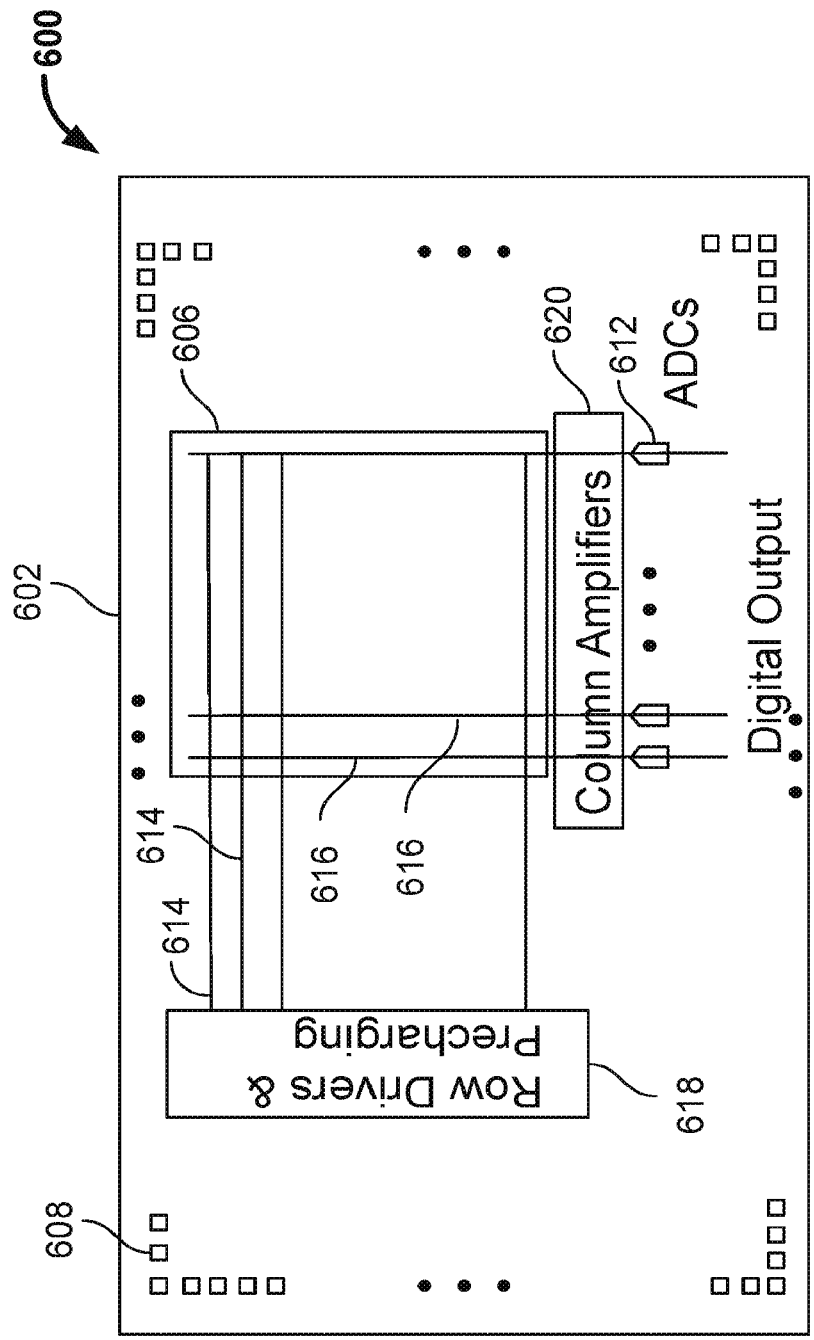
FIG. 6 illustrates an example of a nanopore cell array including a two-dimensional array of nanopore cells.

FIG. 6 illustrates an example of a nanopore cell array 600 including a two-dimensional array of nanopore cells 608. Nanopore cell array 600 may include thousands or even millions of nanopore cells. For example, in one embodiment, nanopore cell array 600 may include 512×512 nanopore cells arranged in 512 lines and 512 columns. Nanopore cell array 600 may be grouped into different banks 606, where each bank may include a subset of the nanopore cells in nanopore cell array 600. In some embodiments, nanopore cells in each column of nanopore cell array 600 may be grouped together, and the voltage levels at the integration capacitors of the nanopore cells in each column may be sampled and converted by an ADC 612. The nanopore cells in a column may share a same ADC in order to reduce overall area and power consumption of the nanopore sensor chip.

Row drivers and pre-charging circuit 618 may be used to selectively precharge nanopore cells in one or more rows (e.g., by closing switch 401 of FIG. 4 to connect the nanopore cells in one or more rows to $V_{pre}$ using row selection lines (or word lines) 614). Row drivers and pre-charging circuit 618 may also be used to sequentially select each row using row selection lines (i.e., word lines) 614. The signals from the nanopore cells on the selected row may be coupled to corresponding column lines 616 (e.g., through a transistor and switch (not shown)). The voltage signals from the nanopore cells on the selected row may be optionally processed (e.g., sensed and amplified) by corresponding column amplifiers 620, and converted to digital outputs by corresponding ADCs 612. In some embodiments, multiple columns could be served by the same column amplifier and ADC.

Figure 7:
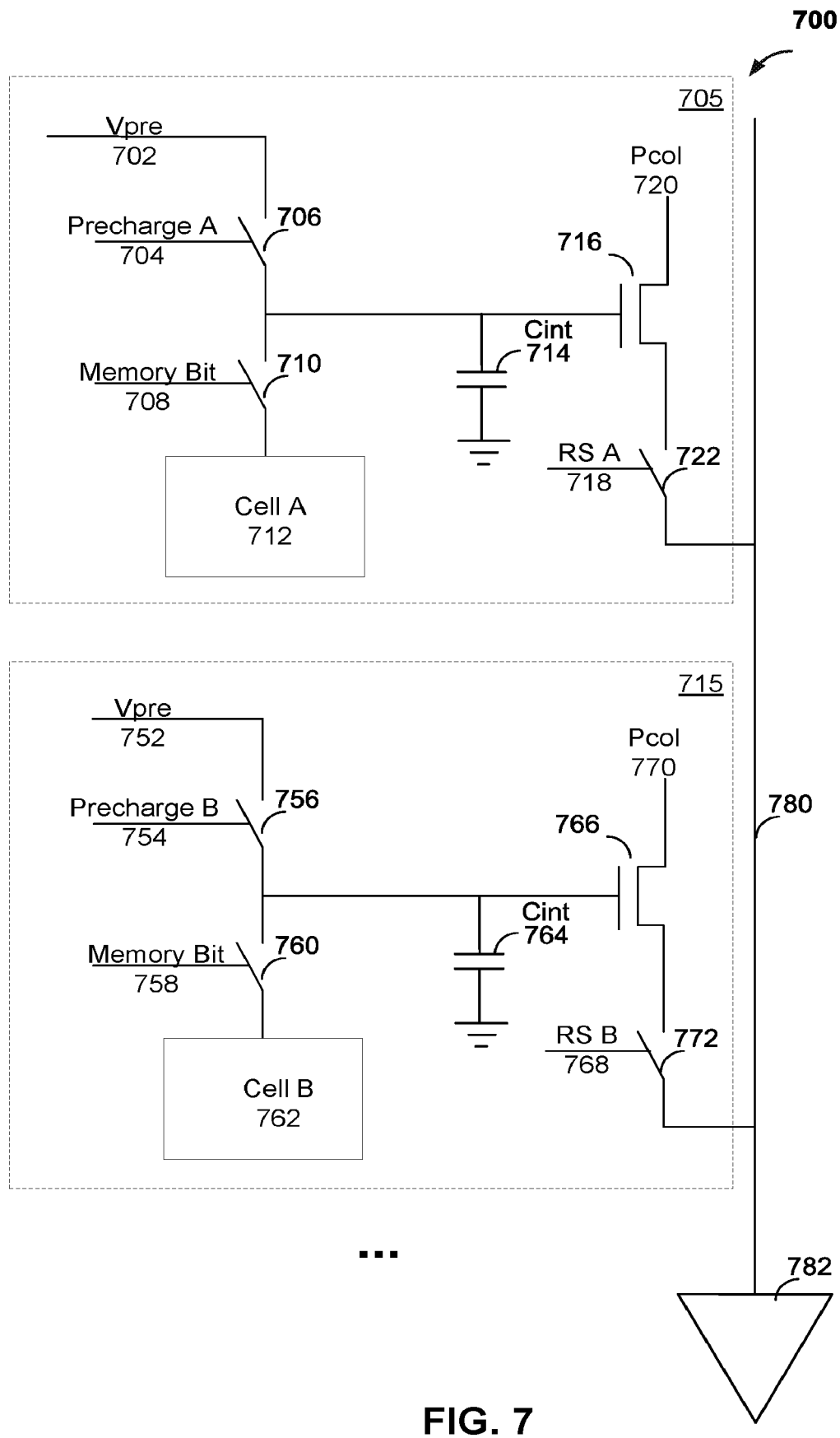
FIG. 7 illustrates a simplified circuit of nanopore cells on a column of a nanopore sensor chip including a two-dimensional array of nanopore cells.

FIG. 7 illustrates a simplified circuit 700 of nanopore cells on a column of a nanopore sensor chip including a two-dimensional array of nanopore cells. Circuit 700 includes two or more nanopore cells 705, 715, etc. on a column of the two-dimensional array. Nanopore cell 705 may include a cell A (712). As described above with respect to FIG. 4, cell A (712) may include a working electrode (e.g., working electrode 402), a counter electrode (e.g., counter electrode 440), a bilayer capacitor (e.g., capacitor 426 ($C_{Bilayer}$)) that models a capacitance associated with a bilayer, a resistor $R_{pore}$ (e.g., resistor $R_{pore}$ 428) that models a variable resistance associated with the nanopore, and a double layer capacitor (e.g., $C_{dbl}$ 424) representing the electrical properties of working electrode and the well (e.g., well 205) of the cell.

Nanopore cell 705 may also include a switch 706 controlled by a precharge A signal 704. Switch 706 can connect nanopore cell 705 to a voltage source $V_{pre}$ 702 to charge nanopore cell 705. A pass device 710 is used to connect or disconnect cell A (712) to voltage source $V_{pre}$ 702 and/or a measurement circuit (described below). Pass device 710 may be controlled by a memory bit 708. The measurement circuit may include an on-chip integration capacitor $C_{int}$ 714 and a read-out circuit. Integration capacitor $C_{int}$ 714 may be precharged by voltage source $V_{pre}$ 702 through switch 706. In some embodiments, voltage source $V_{pre}$ 702 provides a constant voltage with a magnitude of, for example, 900 mV. When switch 706 (and/or pass device 710) are closed, integration capacitor $C_{int}$ 714 (and/or cell A (712)) may be precharged to the voltage level of voltage source $V_{pre}$ 702.

After integration capacitor $C_{int}$ 714 is precharged, precharge A signal 704 may be used to open switch 706 such that integration capacitor $C_{int}$ 714 is disconnected from voltage source $V_{pre}$ 702. At this point, depending on the level of a voltage source (e.g., voltage source $V_{liq}$ 420) on the counter electrode of cell A (e.g., counter electrode 440), integration capacitor $C_{int}$ 714 may be charged or discharged for a fixed integration period as described above with respect to FIGS. 4 and 5.

After the integration period, the voltage level of integration capacitor $C_{int}$ 714 can be read out through the read-out circuit and converted to a digital signal. For example, during the read-out period, pass device 710 may be opened, and a switch 722 of the read-out circuit may be closed under the control of a row select (RS) A signal 718. Thus, the voltage level of integration capacitor $C_{int}$ 714 can be sampled by a column amplifier and ADC circuit 782 through a read-out transistor 716 of the read-out circuit and a column bus 780. In some embodiments, read-out transistor 716 is connected to a column power source Pcol 720, is implemented as a source follower, and may function as a voltage buffer that has a current amplification capability. Thus, read-out transistor 716 may act as a buffer amplifier for isolating integration capacitor $C_{int}$ 714 from noise on a column bus 780 and switch 722.

Other nanopore cells in the column may have the same circuitry as nanopore cell 705. For example, nanopore cell 715 may include a cell B (762), a switch 756 controlled by a precharge B signal 754 for connecting nanopore cell 715 to a voltage source $V_{pre}$ 752, and a measurement circuit including an integration capacitor $C_{int}$ 764 and a read-out circuit that may include a read-out transistor 766 and a switch 772. Voltage source $V_{pre}$ 752 may be used to charge integration capacitor $C_{int}$ 764 and/or cell B (762). A pass device 760 may be used to connect or disconnect cell B (762) to voltage source $V_{pre}$ 752 or the measurement circuit. Pass device 760 may be controlled by a memory bit 758. Integration capacitor $C_{int}$ 764 may be precharged by voltage source Vpre 702 through switch 756 to the voltage level of voltage source $V_{pre}$ 752. After integration capacitor $C_{int}$ 764 is precharged, precharge B signal 754 may be used to open switch 756 such that integration capacitor $C_{int}$ 764 is disconnected from voltage source $V_{pre}$ 752. Depending on the level of a voltage source (e.g., voltage source $V_{liq}$ 420) on the counter electrode of cell B (e.g., counter electrode 440), integration capacitor $C_{int}$ 764 may be charged or discharged for a fixed integration period as described above with respect to FIGS. 4 and 5.

After the integration period, the voltage level of integration capacitor $C_{int}$ 764 can be read out and converted to a digital signal. During the read-out period, switch 772 may be closed under the control of an RS B signal 768. Thus, the voltage level of integration capacitor $C_{int}$ 764 can be sampled by column amplifier and ADC circuit 782 through read-out transistor 766 and column bus 780. Read-out transistor 766 may be similar to read-out transistor 716, and may be connected to a column power source Pcol 770.

Other nanopore cells on the same column may function similarly. As shown in FIG. 7, each nanopore cell (e.g., 705 or 715) may include its own analog components, such as the integration capacitor (e.g., integration capacitor $C_{int}$ 714 or 764) and read-out transistor (e.g., read-out transistor 716 or 766). The integration capacitor may need to be large enough to reduce the noise on the nanopore cell. The read-out transistor may need to be large enough to reduce, for example, the flicker noise and the offset of the read-out transistor (which may limit the minimum range or the dynamic range of the ADC). Therefore, reducing the size of the analog components may affect the performance of the cell. As such, each nanopore cell may need to have a large integration capacitor and read-out transistor, which may limit the minimum size of each nanopore cell.

Figure 8:
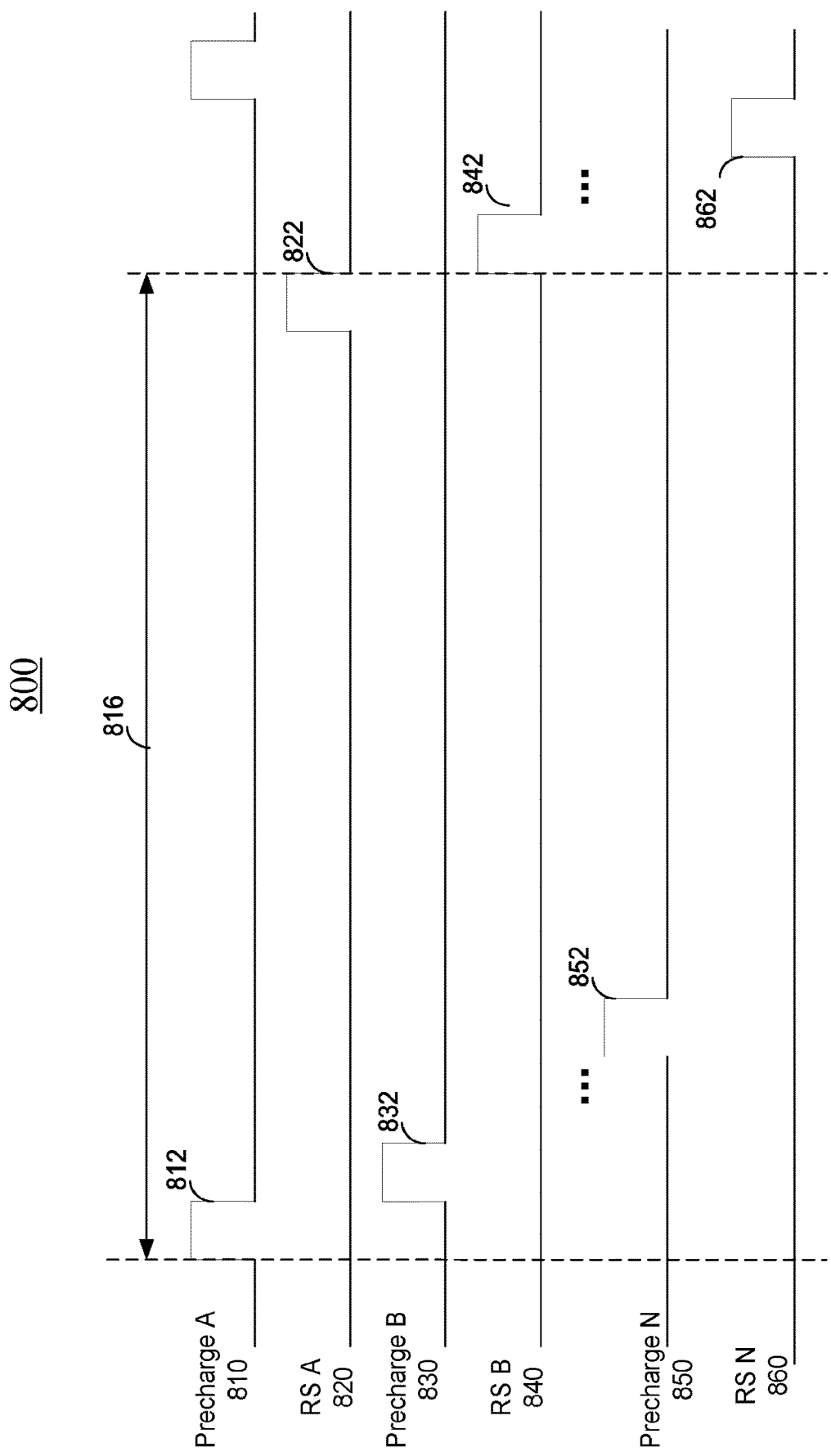
FIG. 8 is a timing diagram illustrating examples of control signals for nanopore cells on a column of a nanopore sensor chip including a two-dimensional array of nanopore cells.

FIG. 8 is a timing diagram 800 illustrating examples of control signals for nanopore cells on a column of a nanopore sensor chip including a two-dimensional array of nanopore cells as described above with respect to FIG. 7. Timing diagram 800 shows examples of control signals including precharge A signal 810, RS A signal 820, precharge B signal 830, RS B signal 840, . . . , precharge N signal 850, and RS N signal 860. The sampling period for each nanopore cell is indicated by a time period 816. Precharge A signal 810 and RS A signal 820 may be used to control the precharge, integration, and read-out for a first nanopore cell (e.g., nanopore cell 705). For example, the integration capacitor of the first nanopore cell (e.g., integration capacitor $C_{int}$ 714) is precharged when a pulse 812 is on precharge A signal 810, which may turn on switch 706.

After pulse 812, the integration capacitor may be charged or discharged by a current signal that relates to the state of the nanopore cell as described above. When a pulse 822 is on RS A signal 820 (e.g., to turn on switch 722), the voltage level of the integration capacitor of the first nanopore cell is read out and converted to a digital signal. Similarly, the integration capacitor of a second nanopore cell (e.g., integration capacitor $C_{int}$ 764) is precharged when a pulse 832 is on precharge B signal 830, e.g., to turn on switch 756. After pulse 832, the integration capacitor may be charged or discharged by a current signal that relates to the state of the nanopore cell as described above. When a pulse 842 is on RS B signal 840 to turn on, for example, switch 772, the voltage level of the integration capacitor of the second nanopore cell is read out and converted to a digital signal. Similarly, precharge N signal 850 and RS N signal 860 may be used to control the precharge, integration, and read-out for the Nth nanopore cell in the column. For example, a pulse 852 on precharge N signal 850 can be used to control the precharge of the integration capacitor on nanopore cell N, and a pulse 862 on RS N signal 860 can be used to control the read-out of the voltage level on the integration capacitor.

III. Nanopore Cell Array with Shared Components

As described above, for a nanopore-based sensor chip, the minimum sampling period may depend on the ADC bandwidth and the digital IO bandwidth, while the integration period of each cell may depend on the size of the integration capacitor for the cell. In many cases, the integration period for a single cell can be less than a half of the sampling period of the sensor chip shown by time period 816. In other words, each cell may only need to use the integration capacitor during a fraction of the sampling period for the precharge, integration, and read-out described above.

According to certain embodiments, multiple nanopore cells can share the same analog components, such as the integration capacitor and the read-out capacitor. For example, if the sampling period is about 1 ms and the integration time for each cell is about 250 μs, four cells may share the same analog components. A small digital switch can be added to each cell to selectively connect the cell to the shared analog components, such as the integration capacitor and the read-out transistor. In one sampling period, each of the cells sharing the same analog components may be precharged, charged or discharged, and read out during a fraction of the sampling period of the sensor chip. The digital components of the cells can be reduced by using more advanced manufacturing technologies that can achieve a smaller critical dimension. In this way, the average size of the nanopore cell can be reduced.

Figure 9:
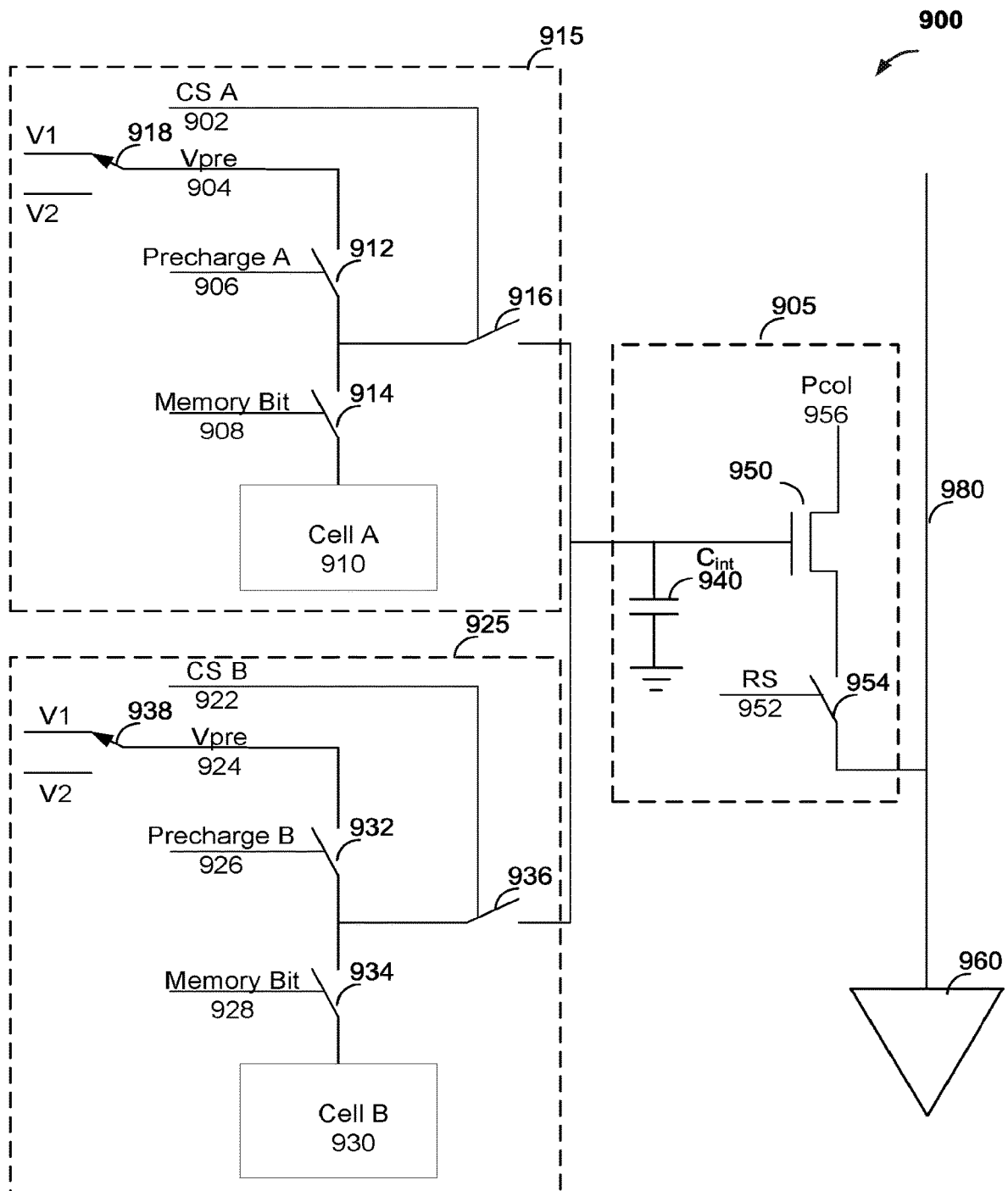
FIG. 9 illustrates a simplified circuit of nanopore cells of a nanopore sensor chip according to certain embodiments.

FIG. 9 is a simplified circuit 900 of nanopore cells of a nanopore sensor chip according to certain embodiments. Circuit 900 includes two or more nanopore cells (e.g., a nanopore cell 915, a nanopore cell 925, etc.) sharing an analog measurement circuit 905 that includes one or more analog components, such as an integration capacitor $C_{int}$ 940 and a read-out transistor 950. Analog measurement circuit 905 may also include a switch 954 that connects integration capacitor $C_{int}$ 940 and read-out transistor 950 to a column amplifier and ADC circuit 960 through a column bus 980. Switch 954 may be controlled by an RS signal 952. Read-out transistor 950 may be similar to read-out transistor 716, and can be connected to a column power source Pcol 956 and form a source follower. Each of the nanopore cells that share some analog components may include a cell, such as cell A (910) or cell B (930). As described above with respect to FIGS. 4 and 7, each cell may include a working electrode (e.g., working electrode 402), a counter electrode (e.g., counter electrode 440), a bilayer capacitor (e.g., capacitor 426 ($C_{Bilayer}$)) that models a capacitance associated with a bilayer, a resistor $R_{pore}$ (e.g., resistor $R_{pore}$ 428) that models a variable resistance associated with the nanopore, and a double layer capacitor (e.g., $C_{dbl}$ 424) representing the electrical properties of working electrode and the well (e.g., well 205) of the cell.

Each nanopore cell may also include a precharge switch (e.g., precharge switch 912 or 932) controlled by a precharge signal (e.g., precharge A signal 906 or precharge B signal 926). The precharge switch can connect the nanopore cell to a voltage source (e.g., $V_{pre}$ signal 904 or $V_{pre}$ signal 924) to precharge the nanopore cell (including the integration capacitor) to a known voltage level. A pass device (e.g., pass device 914 or 934) of the nanopore cell can be used to connect or disconnect the cell (cell A (910) or cell B (930)) to the voltage source or integration capacitor $C_{int}$ 940 and read-out transistor 950. The pass device may be controlled by a memory bit (e.g., memory bit 908 or 928). Each nanopore cell may further include a cell selection switch (e.g., cell selection switch 916 or 936). The cell selection switch may be controlled by a cell selection (CS) signal (e.g., CS A signal 902 or CS B signal 922) to selectively connect each nanopore cell to integration capacitor $C_{int}$ 940 and read-out transistor 950 during different time periods with in a sampling period.

Figure 10:
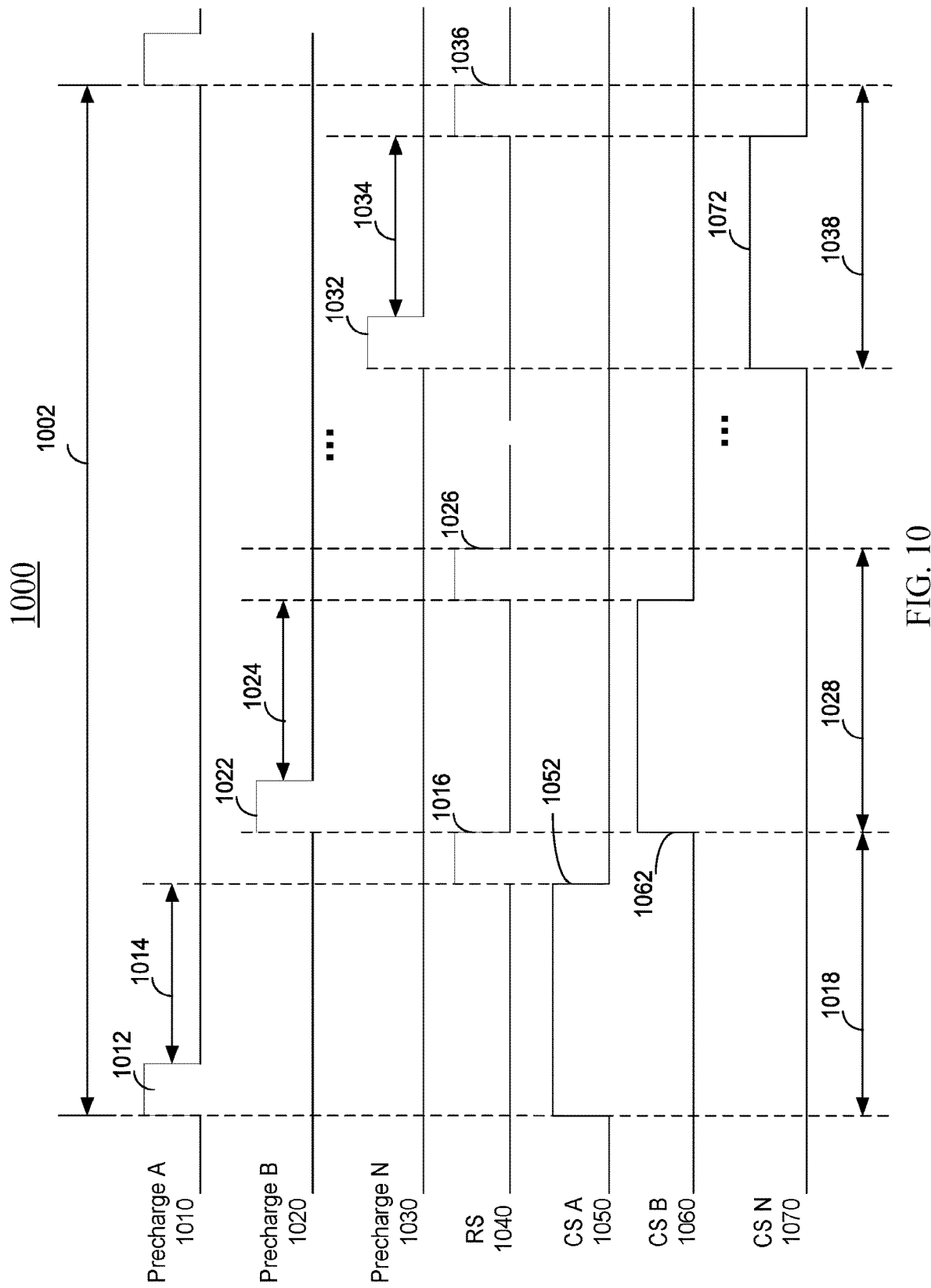
FIG. 10 is a timing diagram illustrating examples of control signals for nanopore cells of a nanopore sensor chip according to certain embodiments.

FIG. 10 is a timing diagram 1000 illustrating examples of control signals for nanopore cells sharing some analog components as described above with respect to FIG. 9 according to certain embodiments. Timing diagram 1000 shows examples of control signals including a precharge A signal 1010, a precharge B signal 1020, ... a precharge N signal 1030, an RS signal 1040, a cell selection (CS) A signal 1050, a CS B signal 1060, and a CS N signal 1070. The sampling period of the sensor chip is indicated by a time period 1002.

When a pulse 1052 (or a high voltage level) is on CS A signal 1050, a cell selection switch (e.g., cell selection switch 916) may be closed, and thus a first nanopore cell (e.g., nanopore cell 915) may be connected to a shared analog measurement circuit (e.g., analog measurement circuit 905) that includes a shared integration capacitor (e.g., shared integration capacitor $C_{int}$ 940). When a pulse 1012 is on precharge A signal 1010 during a precharge period of a first nanopore cell, the precharge switch (e.g., precharge switch 912) and the pass device (e.g., pass device 914) of the first nanopore cell may be closed, and thus the first nanopore cell and the shared integration capacitor $C_{int}$ 940 may be precharged to a voltage level determined by $V_{pre}$ signal 904. After pulse 1012, the precharge switch may be opened, and the first nanopore cell and the shared integration capacitor $C_{int}$ 940 may be discharged or charged by a current that is related to the state of the first nanopore cell, during an integration period 1014. After integration period 1014, the pass device and the cell selection switch for the first nanopore cell may be opened and a pulse 1016 may be applied on RS signal 1040 to turn on switch 954 during a read-out period, such that the voltage level of integration capacitor $C_{int}$ 940 can be read out through column bus 980 and digitized by column amplifier and ADC circuit 960 to generate a measurement value for the first nanopore cell. Thus, the time period 1018 for measuring the first nanopore cell includes the precharge period indicated by pulse 1012, integration period 1014, and the read-out period indicated by pulse 1016.

When a pulse 1062 (or a high voltage level) is on CS B signal 1060, a cell selection switch (e.g., cell selection switch 936) may be closed, and thus a second nanopore cell (e.g., nanopore cell 925) may be connected to the shared analog measurement circuit that includes the shared integration capacitor. When a pulse 1022 is applied on precharge B signal 1020 during a precharge period of a second nanopore cell (e.g., nanopore cell 925), the precharge switch (e.g., precharge switch 932) and the pass device (e.g., pass device 934) of the second nanopore cell may be closed, and thus the second nanopore cell and the shared integration capacitor $C_{int}$ 940 may be precharged to a voltage level determined by $V_{pre}$ signal 924. After pulse 1022, the precharge switch may be opened, and the second nanopore cell and the shared integration capacitor $C_{int}$ 940 may be discharged or charged by a current that is related to the state of the second nanopore cell, during an integration period 1024. After integration period 1024, the pass device and the cell selection switch for the second nanopore cell may be opened and a pulse 1026 may be applied on RS signal 1040 to turn on switch 954, such that the voltage level of integration capacitor $C_{int}$ 940 can be read out through column bus 980 and digitized by column amplifier and ADC circuit 960 to generate a second measurement value for the second nanopore cell. Thus, the time period 1028 for measuring the second nanopore cell includes the precharge period indicated by pulse 1022, integration period 1024, and the read-out period indicated by pulse 1026.

Other nanopore cells that share the same analog components can be similarly connected to the shared analog components (e.g., during a pulse 1072), precharged during a precharge period (e.g., during a pulse 1032), charged or discharged during an integration period (e.g., integration period 1034), and read out during read-out period (e.g., during a pulse 1036). The time period 1038 for measuring the Nth nanopore cell includes the precharge period indicated by pulse 1032, integration period 1034, and the read-out period indicated by pulse 1036. In this way, several nanopore cells may share the same analog components and may be measured during different time periods in a sampling period.

In some embodiments, the cell selection switch and the cell selection signal may not be used, and the pass device can be used to connect each cell to the shared analog components. For example, during the precharge period of a nanopore cell, the precharge switch (e.g., precharge switch 912) and the pass device (e.g., pass device 914) of the nanopore cell may be closed. During the integration period, the precharge switch may be opened and the pass device may be closed. During the read-out period, both the precharge switch and the pass device may be opened. When one nanopore cell is in the precharge, integration, or read-out period, the precharge switches and the pass devices of other nanopore cells sharing the same analog components may be opened. In this way, each nanopore cell sharing the same analog components may be measured independently.

In various embodiments, the signal value of the nanopore cell measured by the analog measurement circuit (e.g., analog measurement circuit 905) may represent any measurable quantity that correlates with the resistivity of a nanopore and from which the resistivity of the nanopore (threaded and/or unthreaded) may be derived. For example, the signal measured by the analog measurement circuit may be (or represent) a voltage or a current signal. The measured signal value may represent the results of a direct measurement of a voltage and/or current or may represent an indirect measurement. For example, the signal value may be a measured duration of time for which it takes a voltage or current to reach a specified value.

In various embodiments, different numbers of nanopore cells, such as 2, 3, 4, 6, 8, 9 or more nanopore cells, may share the same analog components. In some embodiments, the nanopore cells sharing the same analog components may be arranged in a one-dimensional or two-dimensional array. For example, in one embodiment, the nanopore cells sharing the same analog components may be on a same column of the nanopore cell array of the sensor chip.

As shown in FIG. 9, $V_{pre}$ signal 904 or 924 can be connected to one of two or more voltage sources at different voltage levels (e.g., V1 and V2) through a $V_{pre}$ switch (e.g., $V_{pre}$ switch 918 or 938). The $V_{pre}$ switch may selectively connect the working electrode of the nanopore cell to a high voltage level or a low voltage level. For example, the $V_{pre}$ switch may be controlled by an AC control signal, such as a square wave or a rectangular wave signal, such that the working electrode may be connected to the high voltage level during a portion of a cycle of the AC control signal, and may be connected to the low voltage level during another portion of the cycle. The $V_{pre}$ switches may be within the cell or may be outside the cell, for example, at the end of each row.

In some embodiments, the $V_{pre}$ switch may be implemented using two switches controlled by inverse control signals, where one switch may be configured to connect the working electrode to the high voltage level and the other switch may be configured to connect the working electrode to the low voltage level. The AC control signal may be a digital signal, such as a digital clock signal. The high voltage level may be higher than a common signal (e.g., signal $V_{liq}$, and the low voltage level may be lower than the common signal. As such, an AC $V_{pre}$ signal may be effectively applied to the nanopore cell. Different $V_{pre}$ signals may be applied to different nanopore cells by applying different digital AC control signals (e.g., with different levels, periods, or phase delays) to the nanopore cells. In this way, each nanopore cell may be independently controlled. Likewise, rows of nanopore cells can be controlled independently by applying different control signals for different rows of nanopore cells.

In some embodiments, if a nanopore cell is not connected to the integration cap (e.g., integration capacitor $C_{int}$ 940), the nanopore cell may be discharged quickly after being precharged. To avoid the quick discharge, the nanopore cell can be held at a certain voltage level, such as V2, before being charged, discharged, and measured. For example, nanopore cell 915 may be held at voltage level V2 (which may correspond to the dark period during which no data may be measured) by turning on precharge switch 912 and switching $V_{pre}$ switch 918 to connect $V_{pre}$ signal 904 to voltage level V2.

IV. Nanopore Cells without Additional Integration Capacitors

In some embodiments, the parasitic bilayer capacitor (e.g., capacitor 426 ($C_{Bilayer}$)) of the nanopore cell may be used as the integration capacitor and may be large enough for the desired noise performance, and thus no additional integration capacitor may be needed because adding the additional integration capacitor may increase the size of the nanopore cell and reduce the voltage level or increase the integration time. Thus, the analog components shared by a group of nanopore cells may include read-out transistor 950, but may not include integration capacitor $C_{int}$ 940.

In some cases, it may be desirable to check whether the bilayer capacitor is functioning properly. However, it may be difficult to perform the check without using an additional capacitor. Thus, a calibration capacitor may be used for evaluation or verification. In some implementations, a switch may be added to the circuit to disconnect the calibration capacitor during the signal integration and to connect the calibration capacitor to the cell for evaluation or verification purposes. Because the calibration capacitor is disconnected from the cell during the precharge, integration, and read-out periods, it would not affect the measurement result (e.g., the noise in the measurement result) and thus can be made small.

Figure 11:
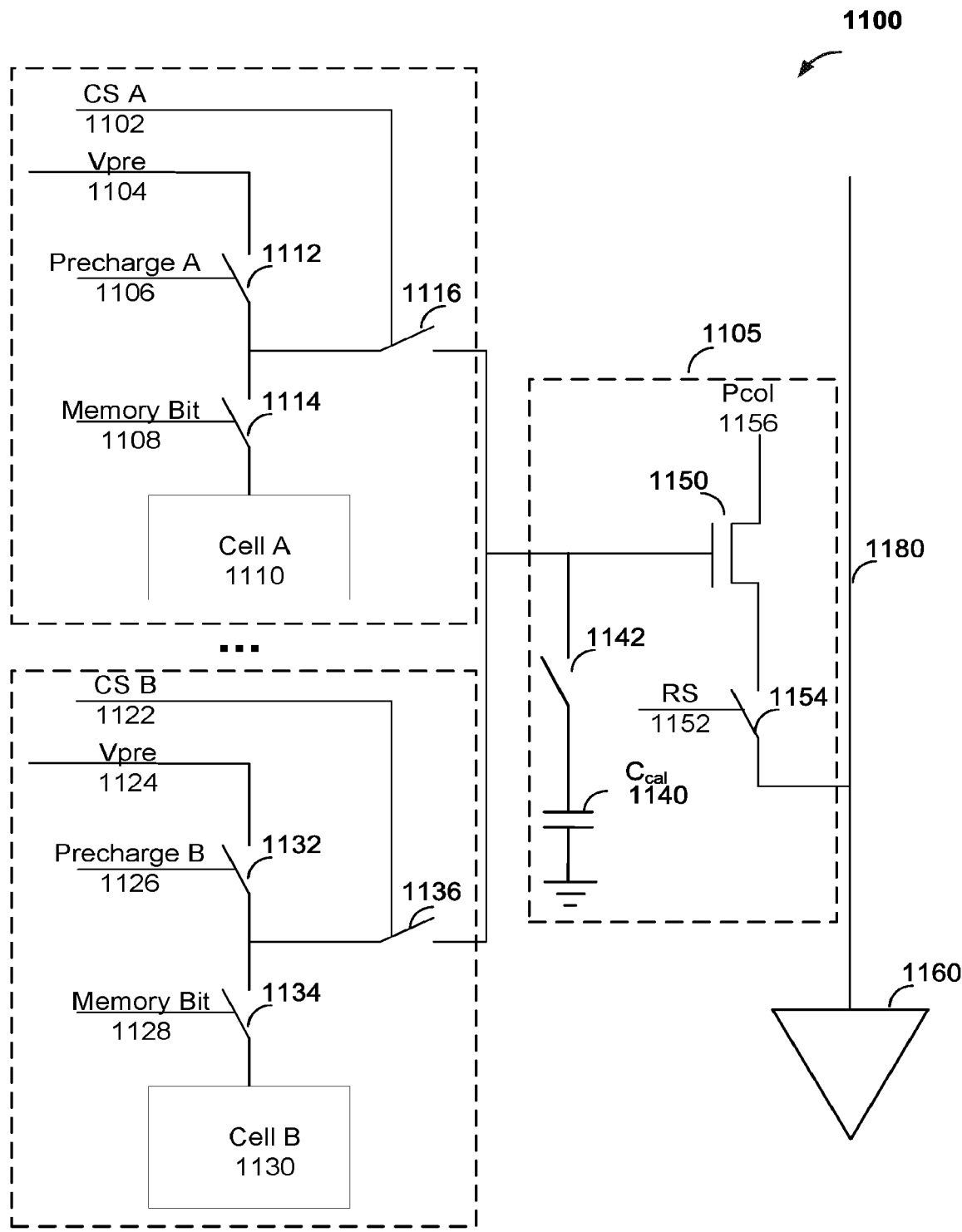
FIG. 11 is a simplified circuit of nanopore cells of a nanopore sensor chip according to certain embodiments.

FIG. 11 is a simplified circuit 1100 of nanopore cells of a nanopore sensor chip according to certain embodiments. Circuit 1100 may include nanopore cells sharing an analog measurement circuit 1105 that includes one or more analog components analog components, such as a calibration capacitor $C_{cal}$ 1140 and a read-out transistor 1150. Analog measurement circuit 1105 may also include a switch 1154 that connects calibration capacitor $C_{cal}$ 1140 and read-out transistor 1150 to a column amplifier and ADC circuit 1160 through a column bus 1180. Switch 1154 may be controlled by an RS signal 1152. Read-out transistor 1150 may be similar to read-out transistor 716, and can be connected to a column power source Pcol 1156 and form a source follower.

Each of the nanopore cells that share some analog components may include a cell, such as cell A (1110) or cell B (1130). Each nanopore cell may also include a precharge switch (e.g., precharge switch 1112 or 1132) controlled by a precharge signal (e.g., precharge A signal 1106 or precharge B signal 1126). The precharge switch can connect the nanopore cell to a voltage source (e.g., $V_{pre}$ 1104 or $V_{pre}$ 1124) to precharge the nanopore cell (e.g., parasitic bilayer capacitor 426 ($C_{Bilayer}$) to a known voltage level. A pass device (e.g., pass device 1114 or 1134) of the nanopore cell can be used to connect the cell (cell A (1110) or cell B (1130)) to the voltage source $V_{pre}$ or calibration capacitor $C_{cal}$ 1140 and read-out transistor 1150. The pass device may be controlled by a memory bit (e.g., memory bit 1108 or 1138).

Each cell may further include a cell selection switch (e.g., cell selection switch 1116 or 1136). The cell selection switch may be controlled by a cell selection signal (e.g., CS A signal 1102 or CS B signal 1122) to selectively connect each cell to calibration capacitor $C_{cal}$ 1140 and read-out transistor 1150 during different time periods within a sampling period. In addition, a switch 1142 may be used to disconnect calibration capacitor $C_{cal}$ 1140 from the rest of the circuit when the nanopore cells are measured in the normal function mode. Calibration capacitor $C_{cal}$ 1140 may be connected to the rest of the circuit when the nanopore cells are measured in the evaluation or verification mode.

Figure 12:
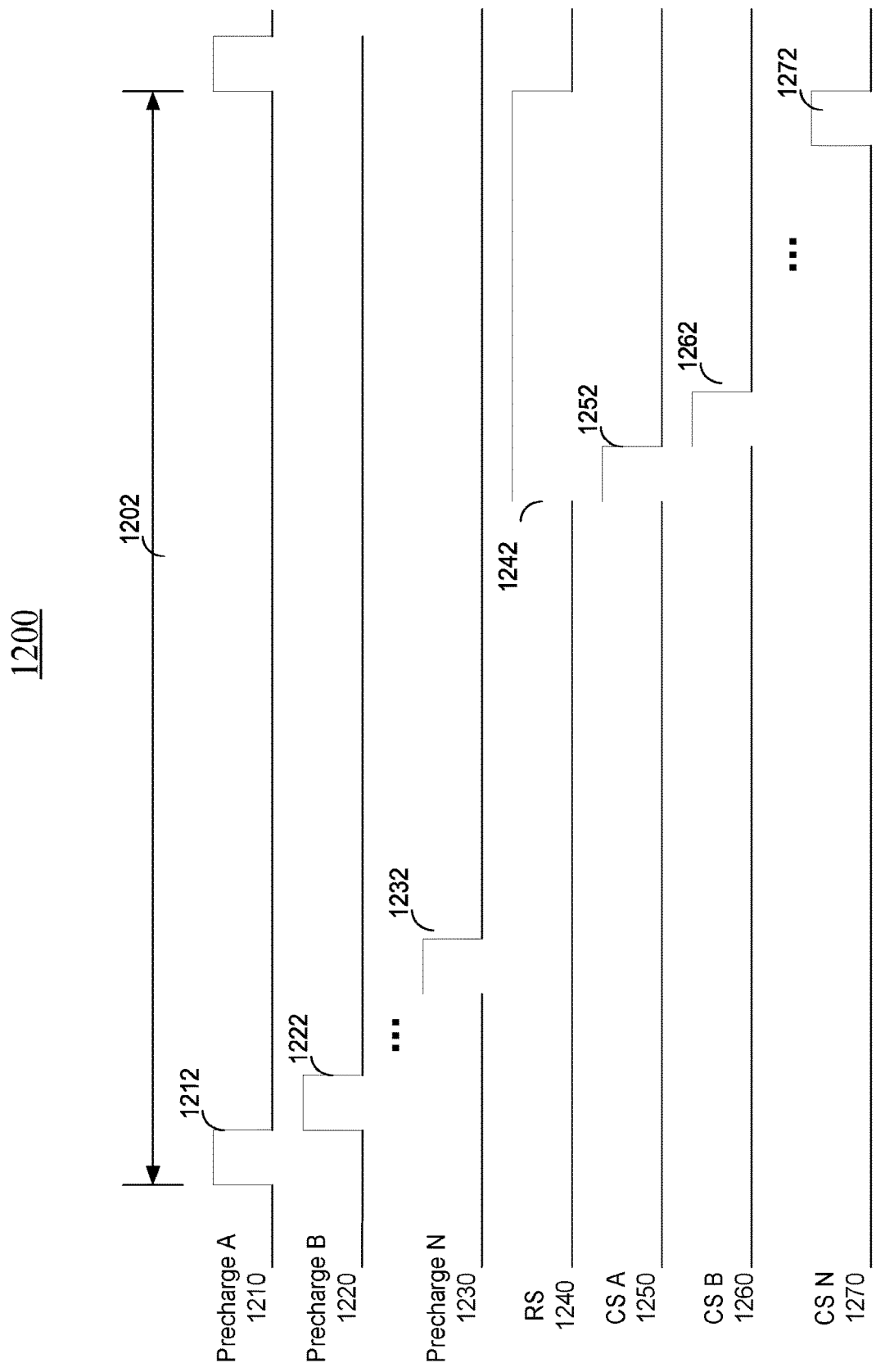
FIG. 12 is a timing diagram illustrating examples of control signals for nanopore cells of a nanopore sensor chip according to certain embodiments.

FIG. 12 is a timing diagram 1200 illustrating examples of control signals for nanopore cells of a nanopore sensor chip as shown in FIG. 11 according to certain embodiments. Timing diagram 1200 shows examples of control signals including a precharge A signal 1210, a precharge B signal 1220, . . . a precharge N signal 1230, an RS signal 1240, a CS A signal 1250, a CS B signal 1260, . . . , and a CS N selection signal 1270. The sampling period of the sensor chip is indicated by a time period 1202. Because no additional integration capacitors are used, the parasitic capacitor (e.g., capacitor 426 ($C_{Bilayer}$)) of the nanopore cells sharing some analog components may be precharged at the same or different times.

For example, when a pulse 1212 is on precharge A signal 1210, precharge switch 1112 may be closed and the parasitic capacitor of nanopore cell A may be precharged. When a pulse 1222 is on precharge B signal 1220, precharge switch 1132 may be closed and the parasitic capacitor of nanopore cell B may be precharged. The parasitic capacitor of nanopore cell N may be precharged when a pulse 1232 is on precharge N signal 1230. Even though FIG. 12 shows no time gap between consecutive pulses 1212, 1222, . . . , and 1232, a time gap may be inserted between any two consecutive pulses. In some embodiments, pulses 1212, 1222, . . . , and 1232 may have no overlap. In some embodiments, pulses 1212, 1222, . . . , and 1232 may at least partially overlap.

After the precharge period (the duration of pulse 1212, 1222, . . . , or 1232), each of the nanopore cell may then be charged or discharged by a current flowing through the corresponding nanopore during the same, overlapping, or non-overlapping time periods. When row selection signal 1240 is at a higher level as shown by a pulse 1242, switch 1154 may be closed to connect read-out transistor 1150 to column amplifier and ADC circuit 1160. When switch 1154 is closed, the voltage levels of the parasitic capacitors on the nanopore cells may be read out one at a time by connecting the nanopore cells to read-out transistor 1150 sequentially using a pulse 1252, a pulse 1262, . . . and a pulse 1272, which may turn on the cell selection switches (e.g., cell selection switches 1116 and 1136) one at a time. Even though FIG. 12 shows no time gap between consecutive pulses 1252, 1262, . . . , and 1272, a time gap may be inserted between any two consecutive pulses.

In the nanopore sensor chip described above with respect to FIGS. 9 and 10, each nanopore cell may be connected to the shared measurement circuit during the precharge, integration, and read-out periods. In contrast, in the nanopore sensor chip described above with respect to FIGS. 11 and 12, each nanopore cell may only be connected to the shared measurement circuit during the read-out period.

V. Example Method

Figure 13:
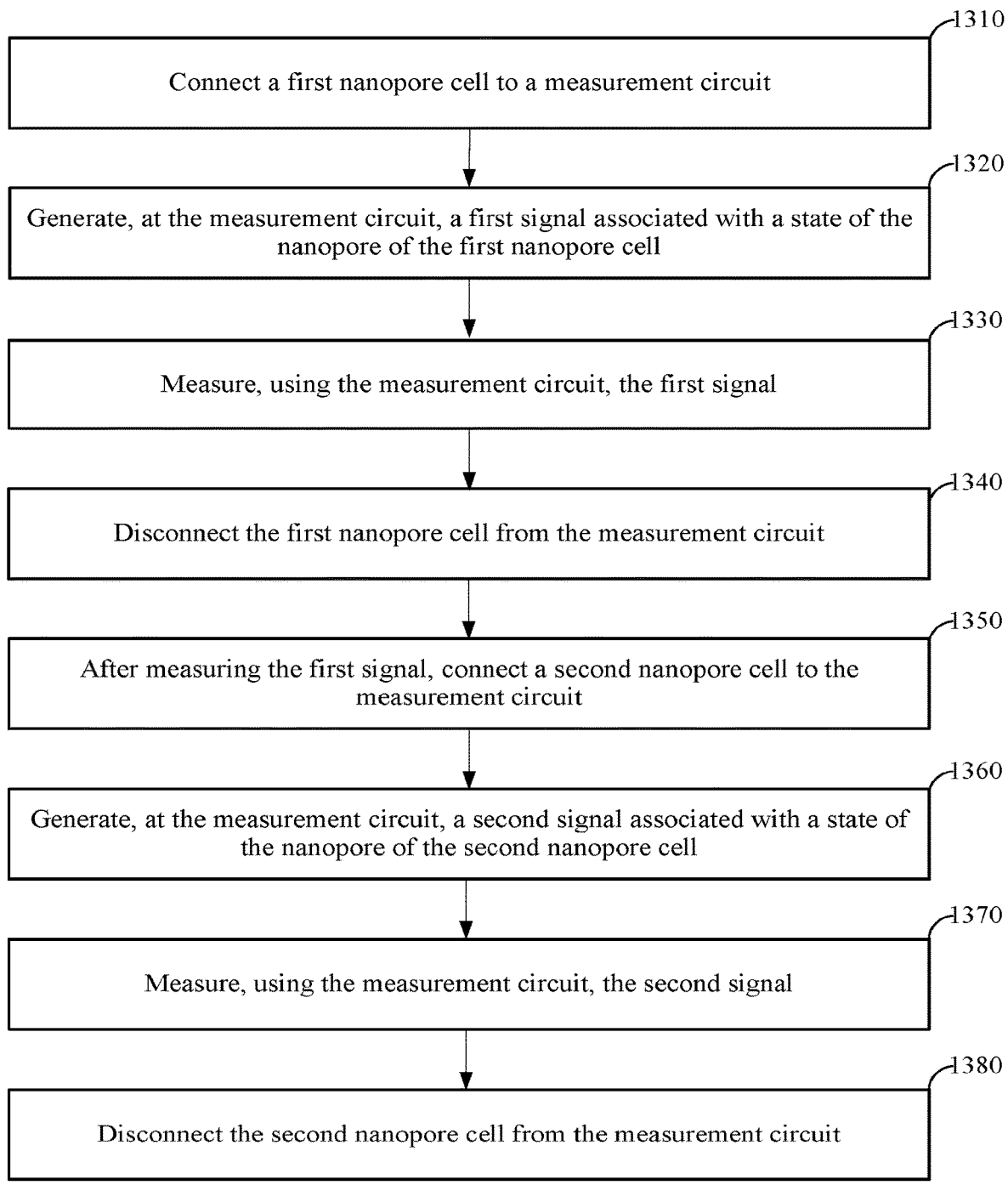
FIG. 13 is a flow chart illustrating an example method of nucleic acid sequencing using a sensor including a set of cells sharing some circuit components according to certain embodiments.

FIG. 13 is a flow chart 1300 illustrating an embodiment of a method of nucleic acid sequencing using a sensor chip including a set of nanopore cells according to certain embodiments. Each of the nanopore cells may include a nanopore as described above. Two or more nanopore cells of the set of nanopore cells may share some analog circuit components as described above with respect to, for example, FIGS. 9-12.

At block 1310, a cell selection switch, such as cell selection switch 916, may connect a first nanopore cell (e.g., first nanopore cell 915) to a measurement circuit (e.g., analog measurement circuit 905). The cell selection switch may be controlled by a cell selection signal (e.g., CS A signal 902). When the first nanopore cell is connected to the measurement circuit, other nanopore cells may be disconnected from the measurement circuit. As described above, in some embodiments, the measurement circuit includes an integration capacitor (e.g., integrator capacitor $C_{int}$ 940), a buffer amplifier (e.g., read-out transistor 950), and a switch (e.g., switch 954) for connecting the integration capacitor to an analog-to-digital conversion circuit (e.g., column amplifier and ADC circuit 960).

At block 1320, a first signal associated with a state of the nanopore of the first nanopore cell may be generated at the measurement circuit. In some embodiments, the integration capacitor may first be precharged to a voltage level, and may then be charged or discharged for an integration period by a current passing through the nanopore of the first nanopore cell. In some embodiments, the integration capacitor may be connected to one of two or more voltage sources through a switch to be precharged to one of two or more voltage levels. The integration time may be less than, for example, one half, one quarter, one eighth of the sampling period of the sensor chip (e.g., 1 ms). The current passing through the nanopore of the first nanopore cell may correlate with the state of the first nanopore cell, such as an open channel or a threading event occurring at the first nanopore cell as described above. The resultant voltage level on the integration capacitor after the integration period may become the first signal.

At block 1330, the measurement circuit and the analog-to-digital conversion circuit may measure the first signal. For example, the switch (e.g., switch 954) may connect the integration capacitor to an analog-to-digital conversion circuit through the buffer amplifier. The switch may be controlled by a row selection signal (e.g., RS signal 952). In some embodiments, the buffer amplifier may include a transistor configured as a source follower. The analog-to-digital conversion circuit may convert the voltage signal read out from the integration capacitor into a digital value, which may be used to determine the state of the first nanopore cell.

At block 1340, the cell selection switch (e.g., cell selection switch 916) may disconnect the first nanopore cell (e.g., first nanopore cell 915) from the measurement circuit (e.g., analog measurement circuit 905). For example, the cell selection switch may be opened under the control of the cell selection signal (e.g., CS A signal 902) to disconnect the measurement circuit from the first nanopore cell.

At block 1350, after the first signal is measured, a second cell selection switch, such as cell selection switch 936, may connect a second nanopore cell (e.g., second nanopore cell 925) to the measurement circuit (e.g., analog measurement circuit 905). The second cell selection switch may be controlled by a second cell selection signal (e.g., CS B signal 922). When the second nanopore cell is connected to the measurement circuit, other nanopore cells may be disconnected from the measurement circuit. In some embodiments, the second nanopore cell and the first nanopore cell are on a same column of the sensor chip At block 1360, a second signal associated with a state of the nanopore of the second nanopore cell may be generated at the measurement circuit. For example, the integration capacitor (e.g., integrator capacitor $C_{int}$ 940) may first be precharged to a voltage level, and may then be charged or discharged for an integration period by a current passing through the nanopore of the second nanopore cell. The current passing through the nanopore of the second nanopore cell may correlate with the state of the second nanopore cell, such as an open channel or a threading event occurring at the second nanopore cell as described above. The resultant voltage level on the integration capacitor after the integration period may become the second signal.

At block 1370, the measurement circuit and the analog-to-digital conversion circuit may measure the second signal. For example, the switch (e.g., switch 954) of the measurement circuit may connect the integration capacitor to the analog-to-digital conversion circuit through the buffer amplifier (e.g., read-out transistor 950) of the measurement circuit. The analog-to-digital conversion circuit may convert the voltage signal read out from the integration capacitor into a digital value, which may be used to determine the state of the second nanopore cell.

At block 1380, the second cell selection switch (e.g., cell selection switch 936) may disconnect the second nanopore cell (e.g., first nanopore cell 925) from the measurement circuit (e.g., analog measurement circuit 905). For example, the second cell selection switch may be opened under the control of the cell selection signal (e.g., CS B signal 922) to disconnect the measurement circuit from the second nanopore cell.

It is noted that even though FIG. 13 describes the operations as a sequential process, many of the operations can be performed in parallel or concurrently. In addition, the order of the operations may be rearranged. For example, in some embodiments, the operations at blocks 1330 and 1340 may be swapped, or the operations at blocks 1370 and 1380 may be swapped. An operation may have additional steps not included in the figure. Some operations may be optional, and thus may be omitted in various embodiments. Some operations described in one block may be performed together with operations at another block. For example, some operations may be performed in parallel. Furthermore, embodiments of the methods may be implemented in hardware, software, firmware, middleware, microcode, hardware description languages, or any combination thereof.

VI. Computer System

Figure 14:
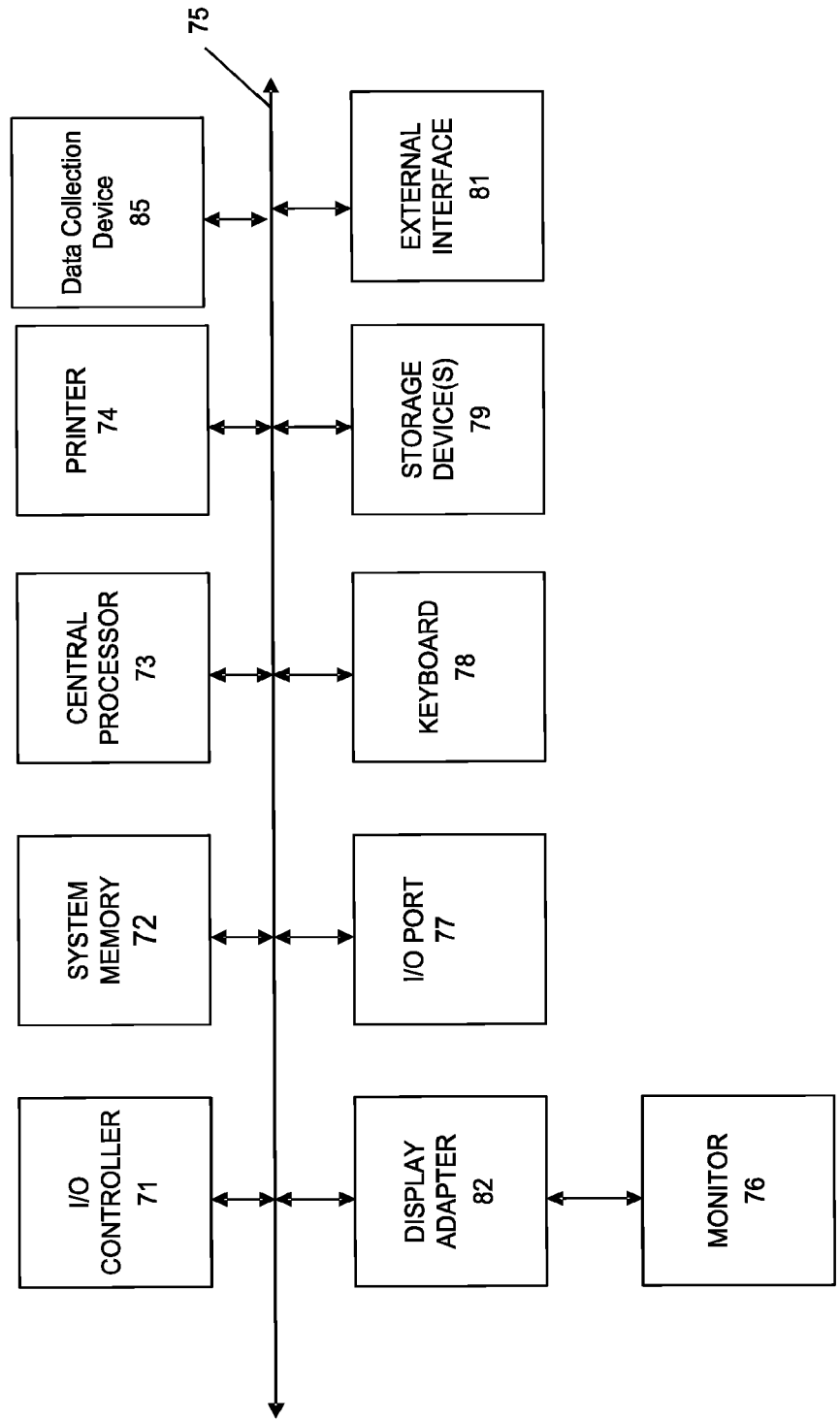
FIG. 14 is a block diagram of an example computer system usable with system and methods, according to certain aspects of the present disclosure.

Any of the computer systems mentioned herein, such as processor 224 and memory 226, digital processor 430, etc., may utilize any suitable number of subsystems. Examples of such subsystems are shown in FIG. 14 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 14 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

What is claimed is:

1. A sensor chip for nucleic acid sequencing, the sensor chip comprising:
   a set of cells, each cell configured to support a nanopore disposed in a membrane;
   a read-out bus for the set of cells;
   a shared analog measurement circuit in electrical communication with the set of cells, wherein the shared analog measurement circuit comprises one or more components and a connect switch that connects the one or more components to an analog-to-digital converter through the read-out bus;
   a set of cell selection switches in electrical communication with both the set of cells and the shared analog measurement circuit; and
   a controller programmed to:
      activate, based on a cell selection signal, a cell selection switch corresponding to a cell of the set of cells during a periodic sampling period of the sensor chip to connect the cell to the shared analog measurement circuit;
      sample for a measurement time using the shared analog measurement circuit an electrical signal generated from the cell; activate, based on a row selection signal, the connect switch to connect the shared analog measurement circuit to the analog-to-digital converter;
      send the sampled electrical signal to the read-out bus through the connect switch; and
      repeat the activations, the sampling, and the sending for another cell of the set of cells during the periodic sampling period.

2. The sensor chip of claim 1, wherein the electrical signal includes a current signal that passes through the nanopore of each cell of the set of cells.

3. The sensor chip of claim 1, wherein the one or more components include an integration capacitor.

4. The sensor chip of claim 1, wherein each cell of the set of cells includes a precharge switch configured to, in combination with a corresponding cell selection switch, connect the cell and the shared analog measurement circuit to a precharge signal.

5. The sensor chip of claim 4, wherein each cell of the set of cells includes a voltage selection switch configured to alternately connect the cell to two precharge voltage levels.

6. The sensor chip of claim 1, wherein the connect switch is a transistor.

7. The sensor chip of claim 6, wherein the transistor is configured as a source follower.

8. The sensor chip of claim 1, further comprising:
   a calibration capacitor; and
   a calibration switch configured to:
      connect the calibration capacitor to the shared analog measurement circuit during cell evaluation; and
      disconnect the calibration capacitor from the shared analog measurement circuit after the cell evaluation.

9. The sensor chip of claim 1, wherein:
   the set of cells are on a same column of the sensor chip; and
   the read-out bus is a column bus of the sensor chip.

10. A method of nucleic acid sequencing using a sensor chip that includes (i) a set of nanopore cells each configured to support a nanopore disposed in a membrane and (ii) a set of cell selection switches in electrical communication with both the set of nanopore cells and one or more components of a shared analog measurement circuit, the method comprising:
    connecting, through a first cell selection switch based on a first cell selection signal, a first nanopore cell of the set of nanopore cells to the shared analog measurement circuit, wherein the shared analog measurement circuit is between the set of nanopore cells and a read-out bus of the sensor chip, wherein the first cell selection switch is activated by a controller of the sensor chip;
    generating, at the shared analog measurement circuit, a first signal associated with a state of the nanopore of the first nanopore cell;
    measuring, via the read-out bus and a connect switch connecting the shared analog measurement circuit to an analog-to-digital converter through the read-out bus, the first signal generated at the shared analog measurement circuit;
    disconnecting the first nanopore cell from the shared analog measurement circuit;
    connecting, through a second cell selection switch based on a second cell selection signal, a second nanopore cell of the set of nanopore cells to the shared analog measurement circuit;
    generating, at the shared analog measurement circuit, a second signal associated with a state of the nanopore of the second nanopore cell;
    measuring, via the read-out bus and the connect switch, the second signal generated at the shared analog measurement circuit; and
    disconnecting the second nanopore cell from the shared analog measurement circuit.

11. The method of claim 10, wherein:
    generating the first signal comprises:
       connecting the first nanopore cell and an integration capacitor of the shared analog measurement circuit to a first precharge voltage source to precharge the integration capacitor and the first nanopore cell;

disconnecting the first nanopore cell and the integration capacitor from the first precharge voltage source; and charging or discharging the integration capacitor by a current signal passing through the nanopore of the first nanopore cell for an integration period to generate the first signal; and generating the second signal comprises:

connecting the second nanopore cell and the integration capacitor to a second precharge voltage source to precharge the integration capacitor and the second nanopore cell;

disconnecting the second nanopore cell and the integration capacitor from the second precharge voltage source; and charging or discharging the integration capacitor by a current signal passing through the nanopore of the second nanopore cell for an integration period to generate the second signal.

12. The method of claim 11, further comprising:
connecting the first and the second precharge voltage sources to a high level signal or a low level signal.

13. The method of claim 11, wherein the integration periods of the first and the second signals are shorter than a half of a sampling period of the sensor chip.

14. The method of claim 10, wherein:
the first signal is a voltage signal; and
measuring the first signal includes measuring the first signal using the analog-to-digital converter through a buffer amplifier.

15. The method of claim 10, further comprising:
connecting, after disconnecting the first nanopore cell from the shared analog measurement circuit, the first nanopore cell to a voltage signal.

16. A method of nucleic acid sequencing using a sensor chip that includes (i) a set of nanopore cells each configured to support a nanopore disposed in a membrane and (ii) a set of cell selection switches in electrical communication with both the set of nanopore cells and one or more components of a shared analog measurement circuit, the method comprising, for each nanopore cell of the set of nanopore cells:

connecting the nanopore cell to the shared analog measurement circuit through a cell selection switch of the set of cell selection switches corresponding to the nanopore cell based on a cell selection signal, wherein the shared analog measurement circuit is between the set of nanopore cells and a read-out bus of the sensor chip, and wherein the cell selection switch of the set of cell selection switches is activated by a controller of the sensor chip;

generating, at the shared analog measurement circuit, a signal associated with a state of the nanopore of the nanopore cell;

measuring, via the read-out bus and a connect switch connecting the shared analog measurement circuit to an analog-to-digital converter through the read-out bus, the signal generated at the shared analog measurement circuit; and disconnecting the nanopore cell from the shared analog measurement circuit.

17. A method of nucleic acid sequencing using a sensor chip that includes (i) a set of nanopore cells each configured to support a nanopore disposed in a membrane and (ii) a set of cell selection switches in electrical communication with both the set of nanopore cells and one or more components of a shared analog measurement circuit, the method comprising:

connecting, through a first cell selection switch based on a first cell selection signal, a first nanopore cell of the set of nanopore cells to the shared analog measurement circuit, wherein:

the sensor chip includes a read-out bus for the set of nanopore cells; the shared analog measurement circuit is connected to an analog-to-digital converter through the read-out bus and a connect switch and is configured to be connected to the set of nanopore cells one at a time; and the first cell selection switch is activated by a controller of the sensor chip;

measuring, using the shared analog measurement circuit, a first signal associated with a state of the nanopore of the first nanopore cell;

disconnecting the first nanopore cell from the shared analog measurement circuit;

connecting a second nanopore cell of the set of nanopore cells to the shared analog measurement circuit;

measuring, using the shared analog measurement circuit, a second signal associated with a state of the nanopore of the second nanopore cell; and disconnecting the second nanopore cell from the shared analog measurement circuit.

18. The method of claim 17, wherein the first signal is a current signal or a voltage signal.

19. The method of claim 17, wherein the shared analog measurement circuit includes an integration capacitor and a buffer.

20. The method of claim 17, wherein measuring the first signal comprises:

connecting the shared analog measurement circuit to the read-out bus.

* * * * *